(12) United States Patent
Gatti McArthur et al.

(10) Patent No.: US 7,361,659 B2
(45) Date of Patent: Apr. 22, 2008

(54) PYRRAZOLO-PYRIMIDINE DERIVATIVES

(75) Inventors: Silvia Gatti McArthur, Basel (CH);
Erwin Goetschi, Reinach (CH);
Juergen Wichmann, Steinen (DE);
Thomas Johannes Woltering, Weil am Rhein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 245 days.

(21) Appl. No.: 11/348,105

(22) Filed: Feb. 6, 2006

(65) Prior Publication Data

US 2006/0183756 A1 Aug. 17, 2006

(30) Foreign Application Priority Data

Feb. 11, 2005 (EP) .................. 05101027

(51) Int. Cl.
*A61K 31/519* (2006.01)
*C07D 487/04* (2006.01)

(52) U.S. Cl. .................. 514/252.16; 514/259.31; 544/281

(58) Field of Classification Search .............. 544/281; 514/259.1, 252.16
See application file for complete search history.

(56) References Cited

U.S. PATENT DOCUMENTS

2003/0139426 A1 7/2003 Wilde et al.

FOREIGN PATENT DOCUMENTS

| EP | 0 891 978 A2 | 1/1999 |
|---|---|---|
| EP | 0891978 B1 | 1/1999 |
| WO | WO 97/29109 A1 | 8/1997 |
| WO | WO02/083652 | 10/2002 |
| WO | WO 03/048132 A2 | 6/2003 |
| WO | WO2004/092135 | 10/2004 |
| WO | WO2005/040171 | 5/2005 |
| WO | WO2005/123738 | 12/2005 |

OTHER PUBLICATIONS

D'Onofrio, et al., J. Neurochem. (Mar. 2003) vol. 84(6) pp. 1288-1295.
Database Chemcats Online, Chemical Abstract Service, Columbus, Ohio, US, XP002316354, downloaded Apr. 2, 2005.
Fraley et al., Bioorg. Med. Chem. Lett., 12, pp. 3537-3541 (2002).

*Primary Examiner*—Brenda Coleman
*Assistant Examiner*—Susanna Moore
(74) *Attorney, Agent, or Firm*—George W. Johnston; Patricia S. Rocha-Tramaloni; Kimberly J. Prior

(57) ABSTRACT

The present invention relates to pyrrazolo-pyrimidine derivatives of formula (I):

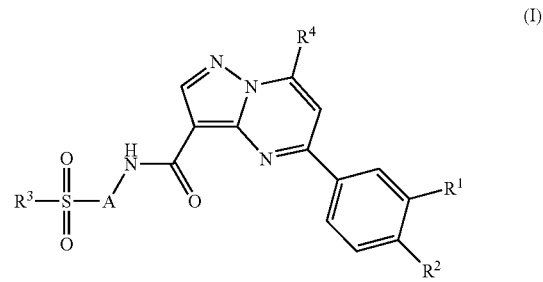

wherein $R^1$ to $R^4$ and A are as defined in the specification, a process for the manufacture thereof, their use for treating or preventing metabotropic glutamate receptors mediated disorders, their use for the preparation of medicaments for treating such disorders and pharmaceutical compositions containing said derivatives.

22 Claims, No Drawings

PYRRAZOLO-PYRIMIDINE DERIVATIVES

PRIORITY TO RELATED APPLICATIONS

This application claims the benefit of European Application No. 05101027.0, filed Feb. 11, 2005, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits. Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, depressions and glioma since mGluR2 antagonists have been found to reduce cell proliferation in human glioma cells (J. Neurochem. March 2003, 84(6): 1288-95).

SUMMARY OF THE INVENTION

The present invention provides pyrrazolo-pyrimidine derivatives of formula (I), a process for the manufacture thereof, their use for treating or preventing metabotropic glutamate receptor mediated disorders, pharmaceutical compositions containing them, and methods for manufacture of such compositions.

In particular, the present invention provides pyrrazolo-pyrimidine derivatives of the general formula (I):

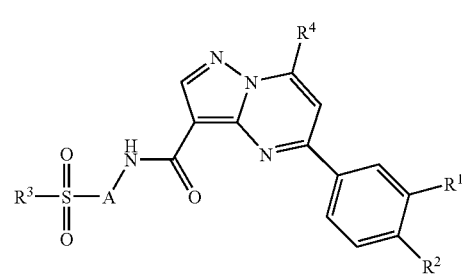

wherein
A is selected from the group consisting of

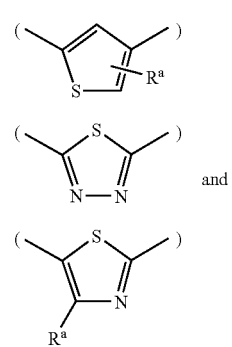

$R^a$ is H, halo or $C_{1-6}$-alkyl;
$R^1$ is H, halo, $C_{1-6}$-alkoxy, $C_{1-6}$-alkyl, $C_{1-6}$-haloalkyl, or $C_{1-6}$-haloalkoxy;
$R^2$ is halogen or $C_{1-6}$-haloalkyl;
$R^3$ is $C_{1-6}$-alkyl optionally substituted by hydroxy;
 or is $NR^bR^c$ wherein $R^b$ and $R^c$ are each independently selected from the group consisting of
H, $C_{3-8}$-cycloalkyl, aryl, heteroaryl having from 5 to 12 ring atoms, and $C_{1-6}$-alkyl which is optionally substituted by one or more substituent(s) selected from the group consisting of halo, hydroxy, $C_{3-8}$-cycloalkyl, aryl, heteroaryl having from 5 to 12 ring atoms and $-NR^{b'}R^{c'}$, wherein $R^{b'}$ and $R^{c'}$ are each independently selected from the group consisting of H and $C_{1-6}$-alkyl;
or $R^b$ and $R^c$ can, together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl; and
$R^4$ is H, straight $C_{1-6}$-alkyl, $C_{1-6}$-haloalkyl or $C_{3-4}$-cycloalkyl;

and pharmaceutically acceptable salts thereof.

The invention includes all racemic mixtures, all their corresponding enantiomers and/or optical isomers. The compounds of formula (I) can also be used in form of their prodrugs. Examples are esters, N-oxides, phosphate esters, glycoamide esters, glyceride conjugates and the like. The prodrugs can add to the value of the present compounds containing compounds of the invention and a pharmaceutically acceptable carrier. The advantages in absorption, pharmacokinetics in distribution and transport to the brain.

Compounds of formula I are metabotropic glutamate receptor antagonists. They can be used for the treatment or prevention of mGLuR5 receptor mediated disorders, such as acute and/or chronic neurological disorders, in particular anxiety and chronic or acute pain selected from the group consisting of restricted brain function caused by bypass operations or transplants, poor blood supply to the brain, spinal cord injuries, head injuries, hypoxia caused by pregnancy, cardiac arrest and hypoglycaemia, chronic and acute pain, Huntington's chorea, amyotrophic lateral sclerosis (ALS), dementia caused by AIDS, eye injuries, retinopathy, idiopathic parkinsonism or parkinsonism caused by medicaments as well as glioma.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

The term "alkyl" denotes a straight-chain or branched saturated hydrocarbon residue with 1 to 6 carbon atoms, preferably with 1 to 4 carbon atoms, such as methyl, ethyl, n-propyl, i-propyl, i-butyl, t-butyl, and the like.

The term "alkoxy" denotes a lower alkyl residue as defined above bound via an oxygen atom. Examples of "lower alkoxy" residues include methoxy, ethoxy, isopropoxy and the like.

The term "halogen" embraces fluorine, chlorine, bromine and iodine.

The terms "alkyl substituted by one or more halogen atoms" and "haloalkyl" each denotes an alkyl residue as defined above wherein at least one hydrogen atom has been replaced with a halogen atom.

The terms "alkoxy substituted by one or more halogen atoms" and "haloalkoxy" each denotes an alkoxy residue as defined above wherein at least one hydrogen atom has been replaced with a halogen atom. Examples of lower alkoxy substituted by one or more halogen include 2,2,2-trifluoroethoxy groups.

The term "alkenyl" used in the present description denotes straight-chain or branched unsaturated hydrocarbon residues with 2-6, preferably 2-4 carbon atoms, such as ethenyl, 2-propenyl, isobutene-1-yl, and those specifically exemplified in the instant patent application.

The term "aryl" represents an aromatic carbocyclic group consisting of one individual ring, or one or more fused rings in which at least one ring is aromatic in nature. Preferred aryl groups are phenyl or naphthyl.

The term "heteroaryl" refers to an aromatic group having 5 to 12 ring atoms and containing one or more heteroatoms selected from nitrogen, oxygen and sulphur. In a certain embodiment, the heteroaryl groups contain one or more nitrogen atoms. Preferred heteroaryl groups have 5 or 6 ring atoms. Examples of such heteroaryl groups are pyridinyl, pyrazinyl, pyrimidinyl or pyridazinyl.

The term "cycloalkyl" means a cycloalkyl group containing 3 to 12, preferably 3 to 8 and still more preferably 3 to 6, carbon atoms, such as cyclopropyl, cyclobutyl, cyclopentyl or cyclohexyl. Cycloalkyl containing 3 to 4 carbon atoms are the most preferred.

The term "a heterocyclic group having 5 to 12 ring atoms" denotes a heterocyclic ring having 5 to 12, preferably 5 to 9 as still more preferably 5 or 6, ring members containing at least one nitrogen atom as ring members, and none, 1, 2 or 3 additional heteroatom ring members selected from N, O and S, the remaining ring members being carbon atoms. Examples of 5 or 6 heterocyclic ring include but are not limited to 1H-tetrazole; 2H-tetrazole; 1,2,3- and 1,24-triazole; imidazole; pyrrole; 1,2,3-, 1,3,4- or 1,2,5-thiadiazole; 1,4-oxazine; 1,2- or 1,4-thiazine; 4-morpholinyl; 1-pyrrolidinyl; 1-piperazinyl, preferably 4-morpholinyl; 1-pyrrolidinyl or 1-piperazinyl.

Substituents for such 5 or 6 membered heterocyclic ring include but are not limited to halo, amino, nitro, cyano, hydroxy, $C_{1-6}$-alkyl optionally substituted by hydroxy, $C_{1-6}$-alkoxy, $C_{2-6}$-alkenyl, $C_{3-8}$-cycloalkyl, or $CF_3$, and preferably $C_{1-6}$-alkyl; or $CF_3$.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable addition salt" refers to any salt derived from an inorganic or organic acid or base.

"Therapeutically effective amount" means an amount that is effective to prevent, alleviate or ameliorate symptoms of disease or prolong the survival of the subject being treated.

The present invention provides pyrrazolo-pyrimidine derivatives of the general formula (I):

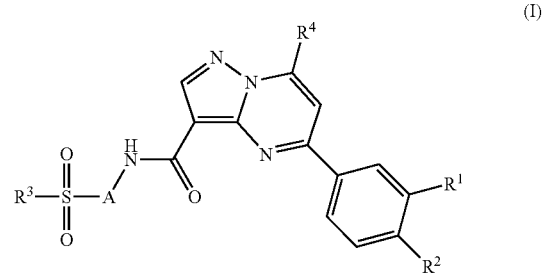

(I)

wherein
A is selected from the group consisting of

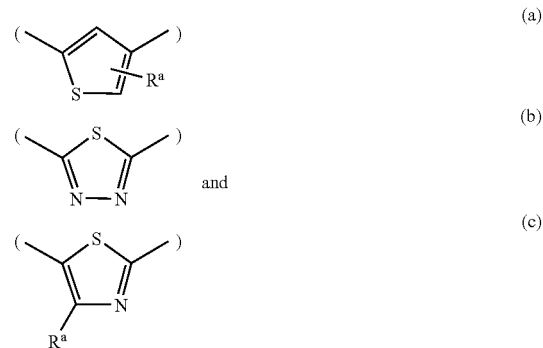

$R^a$ is H, halo or $C_{1-6}$-alkyl;
$R^1$ is H, halo, $C_{1-6}$-alkoxy, $C_{1-6}$-alkyl, $C_{1-6}$-haloalkyl, or $C_{1-6}$-haloalkoxy;
$R^2$ is halogen or $C_{1-6}$-haloalkyl;
$R^3$ is $C_{1-6}$-alkyl optionally substituted by hydroxy;
or is $NR^bR^c$ wherein $R^b$ and $R^c$ are each independently selected from the group consisting of H, $C_{3-8}$-cycloalkyl, aryl, heteroaryl having from 5 to 12 ring atoms, and $C_{1-6}$-alkyl which is optionally substituted by one or more substituent(s) selected from the group consisting of halo, hydroxy, $C_{3-8}$-cycloalkyl, aryl, heteroaryl having from 5 to 12 ring atoms and —$NR^{b'}R^{c'}$, wherein $R^{b'}$ and $R^{c'}$ are each independently selected from the group consisting of H and $C_{1-6}$-alkyl;

or $R^b$ and $R^c$ can, together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl; and $R^4$ is H, straight $C_{1-6}$-alkyl, $C_{1-6}$-haloalkyl or $C_{3-4}$-cycloalkyl;

and pharmaceutically acceptable salts thereof.

The invention includes all racemic mixtures, all their corresponding enantiomers and/or optical isomers. The compounds of formula (I) can also be used in form of their prodrugs.

Examples are esters, N-oxides, phosphate esters, glycoamide esters, glyceride conjugates and the like. The prodrugs can add to the value of the present compounds containing compounds of the invention and a pharmaceutically acceptable carrier. The advantages in absorption, pharmacokinetics in distribution and transport to the brain.

Preferred compounds of the invention are those compounds wherein:
A is selected from the group consisting of

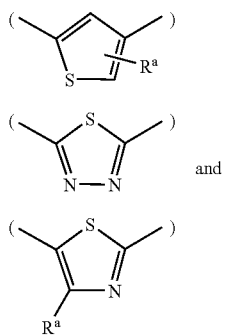

$R^a$ is H, halo, preferably Cl, or $C_{1-6}$-alkyl, preferably methyl;

$R^1$ is H, halo, preferably Cl; $C_{1-6}$-alkoxy, preferably MeO or EtO; $C_{1-6}$-alkyl, preferably methyl; $C_{1-6}$-haloalkyl, preferably $CHF_2$ or $CF_3$; $C_{1-6}$-haloalkoxy, preferably $CF_3CH_2O$;

$R^2$ is halogen, preferably Cl, or $C_{1-6}$-haloalkyl, preferably $CF_3$;

$R^3$ is $NR^bR^c$ wherein $R^b$ and $R^c$ are each independently selected from the group consisting of H, $C_{1-6}$-alkyl, preferably methyl, ethyl, i-propyl, or t-butyl, each of which is optionally substituted by one or more substituent(s) selected from the group consisting of hydroxy and —$NR^{b'c'}$, wherein $R^{b'}$ and $R^{c'}$ are each independently selected from the group consisting of H and $C_{1-6}$-alkyl, preferably methyl; and $R^4$ is $C_{1-6}$-haloalkyl, preferably $CHF_2$ or $CF_3$, or $C_{3-4}$-cycloalkyl, preferably cyclopropyl;

and pharmaceutically acceptable salts thereof.

More particularly, the invention provides compounds in which
A is selected from the group consisting of

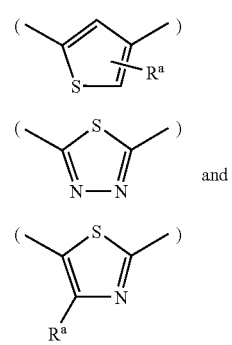

$R^a$ is H, Cl, or methyl;
$R^1$ is H, Cl, MeO, EtO, methyl, $CHF_2$, $CF_3$, or $CF_3CH_2O$;
$R^2$ is Cl, or $CF_3$;
$R^3$ is $NR^bR^c$ wherein $R^b$ and $R^c$ are each independently selected from the group consisting of H, methyl, ethyl, i-propyl, or t-butyl, each of which is optionally substituted by one or more substituent selected from the group consisting of hydroxy and —$NR^{b'c'}$, wherein $R^{b'}$ and $R^{c'}$ are each independently selected from the group consisting of H and methyl; and
$R^4$ is $CHF_2$, $CF_3$, or cyclopropyl;

and pharmaceutically acceptable salts thereof.

Also encompassed by the compounds of formula (I) are those of formula (Ia):

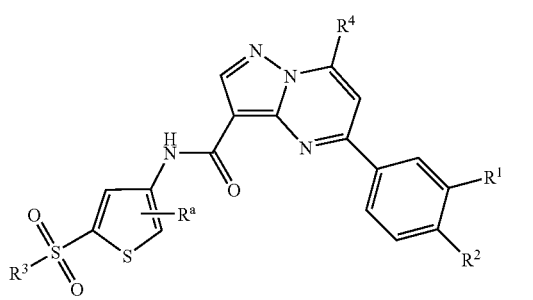

wherein $R^a$, $R^1$, $R^2$, $R^3$ and $R^4$ are as defined hereinabove for formula (I), and pharmaceutically acceptable salts thereof.

Examples of compounds of formula (Ia) include
7-Difluoromethyl-5-(4-trifluoromethyl-phenyl)-pyrazolo[1,5-a]pyrimidine-3-carboxylic acid (2-chloro-5-sulfamoyl-thiophen-3-yl)-amide;
7-Trifluoromethyl-5-(4-trifluoromethyl-phenyl)-pyrazolo[1,5-a]pyrimidine-3-carboxylic acid (2-chloro-5-sulfamoyl-thiophen-3-yl)-amide;
7-Difluoromethyl-5-(4-trifluoromethyl-phenyl)-pyrazolo[1,5-a]pyrimidine-3-carboxylic acid [2-chloro-5-(2-hydroxy-1,1-dimethyl-ethylsulfamoyl)-thiophen-3-yl]-amide;
7-Trifluoromethyl-5-(4-trifluoromethyl-phenyl)-pyrazolo[1,5-a]pyrimidine-3-carboxylic acid [2-chloro-5-(2-hydroxy-1,1-dimethyl-ethylsulfamoyl)-thiophen-3-yl]-amide;

5-(4-Chloro-phenyl)-7-trifluoromethyl-pyrazolo[1,5-a]pyrimidine-3-carboxylic acid (2-chloro-5-sulfamoyl-thiophen-3-yl)-amide;
5-(3-Ethoxy-4-trifluoromethyl-phenyl)-7-trifluoromethyl-pyrazolo[1,5-a]pyrimidine-3-carboxylic acid (2-chloro-5-sulfamoyl-thiophen-3-yl)-amide;
5-(3-Methyl-4-trifluoromethyl-phenyl)-7-trifluoromethyl-pyrazolo[1,5-a]pyrimidine-3-carboxylic acid (2-chloro-5-sulfamoyl-thiophen-3-yl)-amide;
5-(4-Chloro-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
5-(3-Ethoxy-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
5-(3-Methyl-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
5-[3-(2,2,2-Trifluoro-ethoxy)-4-trifluoromethyl-phenyl]-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
5-(3-Chloro-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
7-Difluoromethyl-5-(4-trifluoromethyl-phenyl)-pyrazolo[1,5-a]pyrimidine-3-carboxylic acid [2-chloro-5-(2-hydroxy-1-hydroxymethyl-ethylsulfamoyl)-thiophen-3-yl]-amide;
7-Trifluoromethyl-5-(4-trifluoromethyl-phenyl)-pyrazolo[1,5-a]pyrimidine-3-carboxylic acid [2-chloro-5-(2-hydroxy-1-hydroxymethyl-ethylsulfamoyl)-thiophen-3-yl]-amide;
7-Difluoromethyl-5-(4-trifluoromethyl-phenyl)-pyrazolo[1,5-a]pyrimidine-3-carboxylic acid {5-[bis-(2-hydroxy-ethyl)-sulfamoyl]-2-chloro-thiophen-3-yl}-amide;
7-Trifluoromethyl-5-(4-trifluoromethyl-phenyl)-pyrazolo[1,5-a]pyrimidine-3-carboxylic acid {5-[bis-(2-hydroxy-ethyl)-sulfamoyl]-2-chloro-thiophen-3-yl}-amide;
7-Trifluoromethyl-5-(4-trifluoromethyl-phenyl)-pyrazolo[1,5-a]pyrimidine-3-carboxylic acid [2-chloro-5-(2-hydroxy-ethylsulfamoyl)-thiophen-3-yl]-amide;
7-Difluoromethyl-5-(4-trifluoromethyl-phenyl)-pyrazolo[1,5-a]pyrimidine-3-carboxylic acid [2-chloro-5-(2-hydroxy-1-hydroxymethyl-1-methyl-ethylsulfamoyl)-thiophen-3-yl]-amide;
7-Trifluoromethyl-5-(4-trifluoromethyl-phenyl)-pyrazolo[1,5-a]pyrimidine-3-carboxylic acid [2-chloro-5-(2-hydroxy-1-hydroxymethyl-1-methyl-ethylsulfamoyl)-thiophen-3-yl]-amide;
7-Difluoromethyl-5-(4-trifluoromethyl-phenyl)-pyrazolo[1,5-a]pyrimidine-3-carboxylic acid [2-chloro-5-(2-hydroxy-ethylsulfamoyl)-thiophen-3-yl]-amide;
7-Trifluoromethyl-5-(4-trifluoromethyl-phenyl)-pyrazolo[1,5-a]pyrimidine-3-carboxylic acid (2-methyl-5-sulfamoyl-thiophen-3-yl)-amide;
7-Difluoromethyl-5-(4-trifluoromethyl-phenyl)-pyrazolo[1,5-a]pyrimidine-3-carboxylic acid (2-methyl-5-sulfamoyl-thiophen-3-yl)-amide;
7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-2-methyl-thiophen-3-yl]-amide;
7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-2-methyl-thiophen-3-yl]-amide;
7-Difluoromethyl-5-(4-trifluoromethyl-phenyl)-pyrazolo[1,5-a]pyrimidine-3-carboxylic acid [2-chloro-5-(2-dimethylamino-ethylsulfamoyl)-thiophen-3-yl]-amide;
7-Trifluoromethyl-5-(4-trifluoromethyl-phenyl)-pyrazolo[1,5-a]pyrimidine-3-carboxylic acid [2-chloro-5-(2-dimethylamino-ethylsulfamoyl)-thiophen-3-yl]-amide;
5-(3-Ethoxy-4-trifluoromethyl-phenyl)-7-trifluoromethyl-pyrazolo[1,5-a]pyrimidine-3-carboxylic acid [2-chloro-5-(2-hydroxy-ethylsulfamoyl)-thiophen-3-yl]-amide;
5-(4-Chloro-phenyl)-7-cyclopropyl-pyrazolo[1,5-a]pyrimidine-3-carboxylic acid [2-chloro-5-(2-hydroxy-1,1-dimethyl-ethylsulfamoyl)-thiophen-3-yl]-amide;
7-Difluoromethyl-5-(4-trifluoromethyl-phenyl)-pyrazolo[1,5-a]pyrimidine-3-carboxylic acid [5-(2-amino-ethylsulfamoyl)-2-chloro-thiophen-3-yl]-amide;
7-Difluoromethyl-5-(4-trifluoromethyl-phenyl)-pyrazolo[1,5-a]pyrimidine-3-carboxylic acid [(RS)-2-chloro-5-(3-hydroxy-pyrrolidine-1-sulfonyl)-thiophen-3-yl]-amide;
7-Trifluoromethyl-5-(4-trifluoromethyl-phenyl)-pyrazolo[1,5-a]pyrimidine-3-carboxylic acid [(RS)-2-chloro-5-(3-hydroxy-pyrrolidine-1-sulfonyl)-thiophen-3-yl]-amide;
7-Difluoromethyl-5-(4-trifluoromethyl-phenyl)-pyrazolo[1,5-a]pyrimidine-3-carboxylic acid {2-chloro-5-[(2-hydroxy-ethyl)-methyl-sulfamoyl]-thiophen-3-yl}-amide;
7-Difluoromethyl-5-(4-trifluoromethyl-phenyl)-pyrazolo[1,5-a]pyrimidine-3-carboxylic acid [2-chloro-5-(4-methyl-piperazine-1-sulfonyl)-thiophen-3-yl]-amide;
7-Trifluoromethyl-5-(4-trifluoromethyl-phenyl)-pyrazolo[1,5-a]pyrimidine-3-carboxylic acid [2-chloro-5-(4-methyl-piperazine-1-sulfonyl)-thiophen-3-yl]-amide;
7-Trifluoromethyl-5-(4-trifluoromethyl-phenyl)-pyrazolo[1,5-a]pyrimidine-3-carboxylic acid {2-chloro-5-[(2-hydroxy-ethyl)-methyl-sulfamoyl]-thiophen-3-yl}-amide; and
7-Trifluoromethyl-5-(4-trifluoromethyl-phenyl)-pyrazolo[1,5-a]pyrimidine-3-carboxylic acid [5-(2-amino-ethylsulfamoyl)-2-chloro-thiophen-3-yl]-amide.

Also encompassed by the compounds of formula (I) are those of formula (Ib):

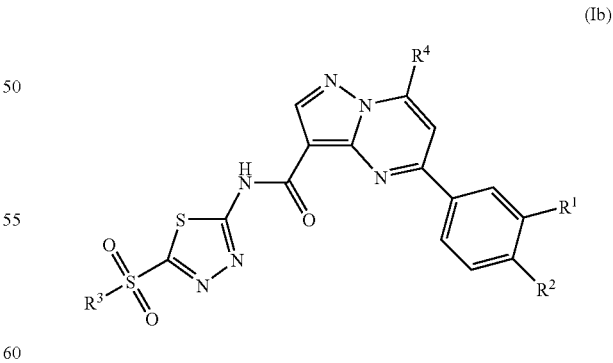

(Ib)

wherein $R^1$, $R^2$, $R^3$ and $R^4$ are as defined hereinabove for formula (I), and pharmaceutically acceptable salts thereof. Examples of compounds of formula (Ib) include 7-Difluoromethyl-5-(4-trifluoromethyl-phenyl)-pyrazolo[1,5-a]pyrimidine-3-carboxylic acid (5-sulfamoyl-[1,3,4]thiadiazol-2-yl)-amide; and 7-Trifluoromethyl-5-(4-trifluoromethyl-phenyl)-pyrazolo[1,5-a]pyrimidine-3-carboxylic acid (5-sulfamoyl-[1,3,4]thiadiazol-2-yl)-amide.

Also encompassed by the compounds of formula (I) are those of formula (Ic):

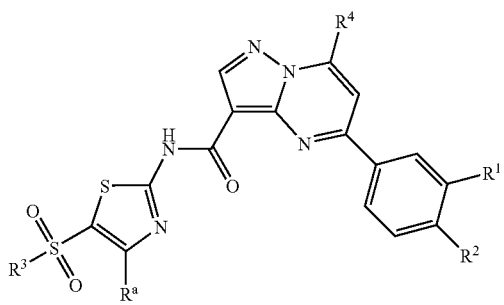

(Ic)

wherein $R^a$, $R^1$, $R^2$, $R^3$ and $R^4$ are as defined hereinabove for formula (I), and pharmaceutically acceptable salts thereof. Examples of compounds of formula (Ic) include 7-Difluoromethyl-5-(4-trifluoromethyl-phenyl)-pyrazolo[1,5-a]pyrimidine-3-carboxylic acid (4-methyl-5-sulfamoyl-thiazol-2-yl)-amide;

7-Trifluoromethyl-5-(4-trifluoromethyl-phenyl)-pyrazolo[1,5-a]pyrimidine-3-carboxylic acid (4-methyl-5-sulfamoyl-thiazol-2-yl)-amide;

7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide;

5-(4-Chloro-phenyl)-7-trifluoromethyl-pyrazolo[1,5-a]pyrimidine-3-carboxylic acid (4-methyl-5-sulfamoyl-thiazol-2-yl)-amide;

5-(3-Ethoxy-4-trifluoromethyl-phenyl)-7-trifluoromethyl-pyrazolo[1,5-a]pyrimidine-3-carboxylic acid (4-methyl-5-sulfamoyl-thiazol-2-yl)-amide;

5-(3-Methyl-4-trifluoromethyl-phenyl)-7-trifluoromethyl-pyrazolo[1,5-a]pyrimidine-3-carboxylic acid (4-methyl-5-sulfamoyl-thiazol-2-yl)-amide;

5-(4-Chloro-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-(3-Ethoxy-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-(3-Methyl-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-(3-Chloro-4-trifluoromethyl-phenyl)-7-trifluoromethyl-pyrazolo[1,5-a]pyrimidine-3-carboxylic acid (4-methyl-5-sulfamoyl-thiazol-2-yl)-amide;

5-(3,4-Dichloro-phenyl)-7-trifluoromethyl-pyrazolo[1,5-a]pyrimidine-3-carboxylic acid (4-methyl-5-sulfamoyl-thiazol-2-yl)-amide;

5-[3-(2,2,2-Trifluoro-ethoxy)-4-trifluoromethyl-phenyl]-7-trifluoromethyl-pyrazolo[1,5-a]pyrimidine-3-carboxylic acid (4-methyl-5-sulfamoyl-thiazol-2-yl)-amide;

5-(3-Chloro-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-(3,4-Dichloro-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-[3-(2,2,2-Trifluoro-ethoxy)-4-trifluoromethyl-phenyl]-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

7-Difluoromethyl-5-(3-methyl-4-trifluoromethyl-phenyl)-pyrazolo[1,5-a]pyrimidine-3-carboxylic acid (4-methyl-5-sulfamoyl-thiazol-2-yl)-amide;

7-Trifluoromethyl-5-(4-trifluoromethyl-phenyl)-pyrazolo[1,5-a]pyrimidine-3-carboxylic acid [2-chloro-5-(2-hydroxy-1-hydroxymethyl-1-methyl-ethylsulfamoyl)-thiophen-3-yl]-amide;

7-Difluoromethyl-5-(3-methyl-4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid {5-[bis-(2-hydroxy-ethyl)-sulfamoyl]-4-methyl-thiazol-2-yl}-amide;

7-Trifluoromethyl-5-(4-trifluoromethyl-phenyl)-pyrazolo[1,5-a]pyrimidine-3-carboxylic acid {5-[bis-(2-hydroxy-ethyl)-sulfamoyl]-4-methyl-thiazol-2-yl}-amide;

7-Trifluoromethyl-5-(4-trifluoromethyl-phenyl)-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-hydroxy-ethylsulfamoyl)-4-methyl-thiazol-2-yl]-amide;

7-Trifluoromethyl-5-(4-trifluoromethyl-phenyl)-pyrazolo[1,5-a]pyrimidine-3-carboxylic acid [5-(2-hydroxy-ethylsulfamoyl)-4-methyl-thiazol-2-yl]-amide;

7-Trifluoromethyl-5-(4-trifluoromethyl-phenyl)-pyrazolo[1,5-a]pyrimidine-3-carboxylic acid (5-sulfamoyl-thiazol-2-yl)-amide;

7-Difluoromethyl-5-(4-trifluoromethyl-phenyl)-pyrazolo[1,5-a]pyrimidine-3-carboxylic acid (5-sulfamoyl-thiazol-2-yl)-amide;

5-(3-Ethoxy-4-trifluoromethyl-phenyl)-7-trifluoromethyl-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-dimethylamino-ethylsulfamoyl)-4-methyl-thiazol-2-yl]-amide;

7-Trifluoromethyl-5-(4-trifluoromethyl-phenyl)-pyrazolo[1,5-a]pyrimidine-3-carboxylic acid [5-(2-dimethylamino-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-thiazol-2-yl]-amide;

7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-thiazol-2-yl]-amide;

5-(4-Chloro-phenyl)-7-cyclopropyl-pyrazolo[1,5-a]pyrimidine-3-carboxylic acid [5-(2-hydroxy-1,1-dimethyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-hydroxy-1-hydroxymethyl-ethylsulfamoyl)-4-methyl-thiazol-2-yl]-amide;

7-Trifluoromethyl-5-(4-trifluoromethyl-phenyl)-pyrazolo[1,5-a]pyrimidine-3-carboxylic acid [5-(2-hydroxy-1-hydroxymethyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [4-methyl-5-(4-methyl-piperazine-1-sulfonyl)-thiazol-2-yl]-amide;

7-Trifluoromethyl-5-(4-trifluoromethyl-phenyl)-pyrazolo[1,5-a]pyrimidine-3-carboxylic acid [4-methyl-5-(4-methyl-piperazine-1-sulfonyl)-thiazol-2-yl]-amide;

7-Difluoromethyl-5-(4-trifluoromethyl-phenyl)-pyrazolo[1,5-a]pyrimidine-3-carboxylic acid {5-[(2-hydroxy-ethyl)-methyl-sulfamoyl]-4-methyl-thiazol-2-yl}-amide;

7-Trifluoromethyl-5-(4-trifluoromethyl-phenyl)-pyrazolo[1,5-a]pyrimidine-3-carboxylic acid {5-[(2-hydroxy-ethyl)-methyl-sulfamoyl]-4-methyl-thiazol-2-yl}-amide;

(RS)-7-Difluoromethyl-5-(4-trifluoromethyl-phenyl)-pyrazolo[1,5-a]pyrimidine-3-carboxylic acid [(RS)-5-(3-hydroxy-pyrrolidine-1-sulfonyl)-4-methyl-thiazol-2-yl]-amide; and 7-Trifluoromethyl-5-(4-trifluoromethyl-phenyl)-pyrazolo[1,5-a]pyrimidine-3-carboxylic acid [(RS)-5-(3-hydroxy-pyrrolidine-1-sulfonyl)-4-methyl-thiazol-2-yl]-amide.

Also encompassed by the compounds of formula (I) are those in which $R^3$ is $C_{1-6}$-alkyl optionally substituted by hydroxyl.

In another embodiment are encompassed compounds of formula (I) in which $R^3$ is $NR^bR^c$ wherein $R^b$ and $R^c$ are independently selected from the group consisting of: H, $C_{3-8}$-cycloalkyl, aryl, heteroaryl having from 5 to 12 ring atoms, and $C_{1-6}$-alkyl which is optionally substituted by one or more substituent(s) selected from the group consisting of halo, hydroxy, $C_{3-8}$-cycloalkyl, aryl, heteroaryl having from 5 to 12 ring atoms and —$NR^{b'}R^{c'}$, wherein $R^{b'}$ and $R^{c'}$ are each independently selected from the group consisting of H and $C_{1-6}$-alkyl; or $R^b$ and $R^c$ can, together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl. Of these, compounds wherein $R^b$ and $R^c$ are hydrogen are preferred. Alternatively, preferred compounds in this embodiment are those in which $R^b$ and $R^c$ are each independently $C_{1-6}$-alkyl, optionally substituted by one or more substituent(s) selected from the group consisting of halo, hydroxy, and $C_{3-8}$-cycloalkyl. As another alternative within this group are those compounds in which $R^b$ and $R^c$ are each independently $C_{1-6}$-alkyl, optionally substituted by —$NR^{b'}R^{c'}$, wherein $R^{b'}$ and $R^{c'}$ are each independently selected from the group consisting of H and $C_{1-6}$-alkyl. As yet another alternative within this group are those compounds in which $R^b$ and $R^c$ together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl.

The compounds of the invention can be prepared according to a process comprising reacting a compound of formula (VI):

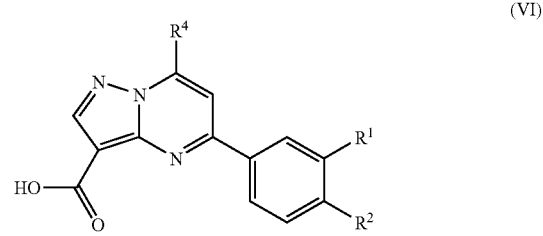

(VI)

with a compound of formula (VII):

(VII)

wherein A, $R^1$, $R^2$, $R^3$ and $R^4$ are as defined in formula (I) above;

to obtain the compound of formula (I), and if desired converting the compound of formula (I) into its pharmaceutically acceptable addition salt.

The pharmaceutically acceptable addition salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formulae (I), (Ia), (Ib) and (Ic).

The synthesis of the intermediate compounds of formula (VI) above can be carried out in accordance with the following general procedure I which procedure is outlined below in scheme 1. As for the reaction of the compound of formula (VII) with the compound of formula (VI), it can be carried out for example in accordance with the following general procedure II which procedure is outlined below in scheme 2. In these schemes, A, $R^1$, $R^2$, $R^3$ and $R^4$ are as defined hereinabove. Procedures I and II are applicable for the preparation of all the compounds according to formulae (I), (Ia), (Ib) and (Ic).

Scheme 1

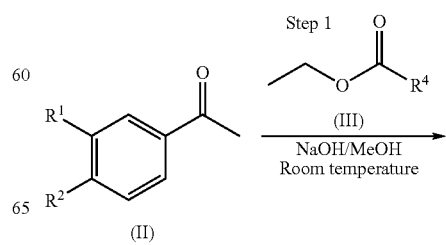

-continued

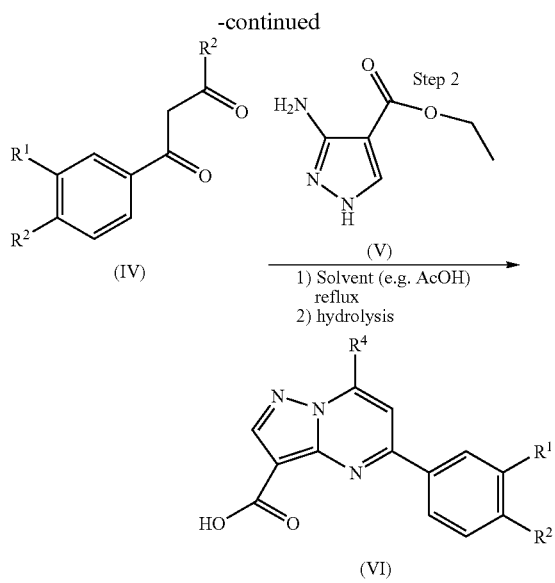

General Procedure I

Step 1:

To a stirred solution of compound of formula (III) in an organic solvent (e.g. tert-butyl-methyl-ether) is added at room temperature a solution of sodium methanolate in methanol followed by a solution of compound of formula (II) in an organic solvent (e.g. tert-butyl-methyl-ether). The reaction mixture is stirred at room temperature for about 19 h, cooled, acidified and extracted (e.g. with diethyl ether). The combined organic layers are washed and dried (e.g. $MgSO_4$) and evaporated to give crude the compound of formula (IV) which can be used without further purification.

Step 2:

A stirred mixture of commercially available 3-amino-4-ethoxycarbonyl-pyrazole (compound of formula (V)) and compound of formula (IV) in an organic acid (e.g. acetic acid) is heated under reflux conditions for about 1.5 h. The reaction mixture is evaporated and the crude product is dissolved in a mixture of a concentrated base (e.g. KOH in methanol and water). The reaction mixture is stirred at about 60° C. for about 1.5 h, cooled, acidified and concentrated. The precipitate is collected by filtration and further purified (e.g. by crystallization from diethylether/methanol) to give the compound of formula (VI).

Scheme 2

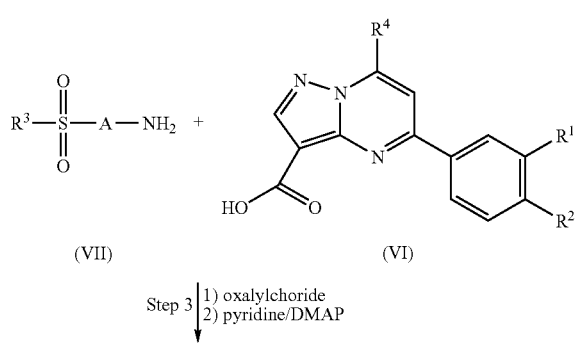

General Procedure II

Step 3:

To a stirred solution of compound of formula (VI) in a solvent (e.g.THF) is added at room temperature DMF, the solution is cooled to about 0° C. and oxalylchloride is added. The reaction mixture is stirred at room temperature for about 3 h and evaporated to dryness. The precipitate is dissolved in pyridine and, while stirring at room temperature, 4-dimethylaminopyridine and a compound of formula (VII) are added. The reaction mixture is allowed to stir at room temperature for about 16 h, evaporated to dryness and the crude product purified (e.g. by flash chromatography on silica gel) to yield the product, which can be further purified (e.g. by crystallization from methanol/hexane).

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or a pharmaceutically acceptable salt thereof and a therapeutically inert excipient are also an object of the present invention, as is a process for the production of such medicaments which comprises bringing one or more compounds of formula (I) or pharmaceutically acceptable salts thereof and, if desired, one or more other therapeutically valuable substances into a galenical dosage form together with one or more therapeutically inert carriers.

The compounds of formula (I) and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia, depression and glioma.

The dosage at which the compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The compounds of the present invention are group II mGlu receptor antagonists. The compounds show activities, as measured in the assay described below, of 0.150 µM or less, typically 0.030 µM or less, and ideally of 0.010 µM or less. In the table below are described some specific Ki values of representative compounds.

| Ex. No. | 2 | 3 | 8 | 35 |
|---|---|---|---|---|
| $K_i$ mGlu2 (µM) | 0.0069 | 0.142 | 0.0025 | 0.027 |

[$^3$H]-LY354740 Binding on mGlu2 Transfected CHO Cell Membranes.

Transfection and Cell Culture cDNA encoding the rat mGlu2 receptor protein in pBluescript II was subcloned into the eukaryotic expression vector pcDNA I-amp from Invitrogen Ltd (Paisley, UK). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco-Invitrogen (Carlsbad, Calif., USA). Selection was made in the presence of G-418 (1000 ug/ml final) and MCPG??. Clones were identified by reverse transcription of 5 µg total RNA, followed by PCR mGlu2 receptor specific primers 5'-atcactgcttgggtttctg-gcactg-3' and 5'-agcatcactgtgggtggcataggagc-3'in 60 mM Tris HCl (pH 10), 15 mM (NH4)$_2$SO$_4$, 2 mM MgCl$_2$, 25 units/ml Taq Polymerase with 30 cycles annealing at 60° C. for 1 min., extention at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the micro BCA method from Pierce-Perbio (Rockford, Ill., USA) using bovine serum albumin as standard.

[$^3$H]-LY354740 Binding

After thawing, the membranes were resuspended in cold 50 mM Tris-HCl buffer containing 2 mM MgCl$_2$ (pH 7) (binding buffer). The final concentration of the membranes in the assays was 25 µg protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/B glass fiber filters and washed 5 times with cold binding buffer. Non specific binding was measured in the presence of 10 µM DCG IV. After transfer of the filters into plastic vials containing 10 ml of Ultima-gold scintillation fluid from Perkin-Elmer(Boston, Mass., USA), the radioactivity was measured by liquid scintillation in a Tri-Carb 2500 TR counter (Packard, Zürich, Switzerland).

Data Analysis.

The inhibition curves were fitted with a four parameter logistic equation giving IC$_{50}$ values, and Hill coefficients.

EXAMPLES

Synthesis of Starting Material

Almost all of the starting materials used in the general procedures I and II are commercially available. The non-commercially available starting materials have been prepared according to the procedures as outlined hereafter and unless otherwise specified, the intermediate compounds described therein are novel compounds. Other starting materials useful in the general procedures I and II can be prepared taking into account the following examples of preparation and using known methods.

A—Synthesis of Acetophenones Derivatives of Formula (II)

Example A.1

4-Methyl-3-trifluoromethyl-acetophenone

To a stirred and cooled (0° C.) solution of potassium tert.-butanolate (1.39 g, 12 mmol) in DMSO (3 ml) was added diethyl malonate (1.9 ml, 12 mmol) and the reaction mixture was stirred for 20 min at room temperature. To the white suspension was added at room temperature 4-fluoro-3-trifluoromethyl-acetophenone (1 g, 5 mmol) and DMSO (2 ml). The reaction mixture was stirred for 6 h at 60° C. and for 16 h at room temperature. The reaction mixture was cooled (0° C.), a solution of potassium hydroxide (1.09 g, 19 mmol) in water (2 ml) was added and the mixture was stirred at 100° C. for 23 h. The mixture was poured into ice/water (40 ml) and extracted with diethyl ether (2×40 ml). The combined organic layers were washed with water (3×30 ml), brine (30 ml), dried (MgSO$_4$) and evaporated. The crude product (0.92 g) was further purified by column chromatography on silica gel (heptane/ethyl acetate 3:1) to give the title compound (0.76 g, 77%) as a light yellow liquid. MS (EI) 202.0 [M].

Example A.2

4-Ethoxy-3-trifluoromethyl-acetophenone

To a stirred suspension of potassium ethanolate (2.36 g, 27 mmol) in ethanol (30 ml) was added at room temperature a solution of 4-fluoro-3-trifluoromethyl-acetophenone (2.5 g, 12 mmol) in ethanol (10 ml). The reaction mixture was stirred at 60° C. for 2 h and evaporated. Ice/2 N HCl (50 ml) was added and the water layer was extracted with diethylether (2×100 ml). The combined organic layers were washed with ice-water (50 ml), brine (50 ml), dried (MgSO$_4$) and evaporated to give the title compound (2.9 g, 98%) as a brown solid, which was used without further purification. MS (EI) 232.1 [M].

Example A.3

4-(2,2,2-Trifluoro-ethoxy)-3-trifluoromethyl-acetophenone

To a stirred solution of 4-fluoro-3-trifluoromethyl-acetophenone (2.5 g, 12 mmol) in DMSO (15 ml) was added at room temperature 2,2,2-trifluoroethanol (1.7 g, 17 mmol) and potassium hydroxide (1.74 g, 27 mmol). The reaction mixture was stirred for 30 min at 40° C., ice/2N HCl (50 ml) was added and the water layer was extracted with diethylether (2×100 ml). The combined organic layers were washed with ice-water (50 ml), brine (50 ml), dried (MgSO$_4$) and evaporated to give the title compound (3.6 g, 98%) as a brown solid, which was used without further purification. MS (EI) 286.1 [M].

Example A.4

3-Methyl-4-trifluoromethyl-acetophenone

The 1-(3-methyl-4-trifluoromethyl-phenyl)-ethanone was prepared by the following sequence:

Step 1: 5-Methyl-2-nitro-4-trifluoromethyl-phenylamine

Under argon atmosphere, a suspension of potassium tert-butanolate (71.6 g, 625 mmol) in DMSO (150 mL) was placed in a 1.5 L flask, fitted with a mechanical stirrer. Then diethyl malonate (97.9 mL, 625 mmol) was added drop wise at 20-30° C. under ice bath cooling. To the thick white suspension was the added solid commercially available 5-chloro-2-nitro-4-trifluoromethyl-phenylamine [CAS-No. 35375-74-7] (60.14 g, 250 mmol) in one portion, the mixture was diluted with DMSO (100 mL) and the red solution warmed up to 60° C. and stirred for 20 h at 60° C. The mixture was cooled to 23° C. and a solution of potassium hydroxide (85%, 65.24 g, 1 mol) in water (100 mL) was added drop wise. The mixture was then heated to 100° C. and stirred for further 4 h. The mixture was cooled to 23° C., diluted with water (ca. 1000 mL), acidified with 37% HCl 3 to pH 3, and extracted three times with tert-butyl methyl ether (TBME) The organic layers were washed with brine, dried over MgSO$_4$ and evaporated to give a brown solid, which was triturated with hot heptane, filtered off and washed with heptane to give the title compound as a brown solid (50.0 g, 91%), which was used without further purification. MS (ISN) 218.9 [M–H].

Step 2: 1-Bromo-5-methyl-2-nitro-4-trifluoromethyl-benzene

To a rapidly stirred mixture of tert-butyl nitrite (45.33 mL, 382 mmol) and copper(II) bromide (76.1 g, 341 mmol) in acetonitrile (450 mL) at 65° C. was added cautiously solid 5-methyl-2-nitro-4-trifluoromethyl-phenylamine from step 1 (50.0 g, 227 mmol). After the addition was complete, stirring was continued for further 1 h at 65° C. The mixture was cooled to 23° C. and poured into 1 N HCl (1000 mL), extracted twice with TBME, the organic layer was washed with brine, dried over MgSO$_4$. Removal of the solvent in vacuum left a brown oil, which was purified by silica gel column chromatography with heptane/ethyl acetate 9:1 to give the title compound as a yellow liquid (49.8 g, 77%). MS (EI) 283.0 [M] and 285.0 [M$^+$2].

Step 3: 5-Methyl-2-nitro-4-trifluoromethyl-benzonitrile

A mixture of 1-bromo-5-methyl-2-nitro-4-trifluoromethyl-benzene from step 2 (49.80 g, 175 mmol) and copper (I) cyanide (16.5 g, 184 mmol) in 1-methyl-2-pyrrolidone (NMP) (180 mL) was heated up to 150° C. and stirred for 30 min under nitrogen atmosphere. The mixture was cooled to 23° C. and poured into 1 N HCl, extracted with TBME, washed with brine and dried over Na$_2$SO$_4$. Removal of the solvent in vacuum left a brown oil, which was purified by silica gel column chromatography with heptane/ethyl acetate 4:1->2:1 to give the title compound as a light yellow solid (35.48 g, 88%). MS (EI) 230.1 [M].

Step 4: 2-Amino-5-methyl-4-trifluoromethyl-benzonitrile

Iron powder (37.42 g, 670 mmol) was added in small portions to a stirred suspension of finely grinded 5-methyl-2-nitro-4-trifluoromethyl-benzonitrile from step 3 (34.58 g, 150 mmol) in methanol (75 mL) and 37% HCl (93 mL). The internal temperature was kept between 40 and 60° C. by external water bath cooling. The resulting brown solution was stirred for 1 h at 50° C., giving a green suspension. The mixture was poured into ice cold water (600 mL), the precipitated solid was filtered off and washed with water to give a green solid, which was dissolved in boiling ethanol (700 mL), activated carbon (ca. 10 g) was added and the mixture was refluxed for 1 h. The hot solution was filtered and the solvent was evaporated in vacuum to leave the title compound as a brown-yellow solid (23.55 g, 78%), which was used without further purification. MS (EI) 200.1 [M].

Step 5: 3-Methyl-4-trifluoromethyl-benzonitrile

To a solution of 2-amino-5-methyl-4-trifluoromethyl-benzonitrile from step 4 (23.34 g, 117 mmol) in dry THF (350 mL) was added isoamyl nitrite (34.3 mL, 257 mmol) and the mixture was refluxed for 20 h. Additional isoamyl nitrite (16.6 mL, 129 mmol) was added and the mixture was refluxed for further 20 h. The mixture was cooled to 23° C. and diluted with TBME, the organic layer was washed with 1 N HCl, sat. NaHCO$_3$-sol. and brine, dried over Na$_2$SO$_4$. Removal of the solvent in vacuum left a brown oil (25.82 g), which was purified by bulb to bulb distillation to give a yellow liquid (20.11 g), which was finally purified by distillation to give the title compound as a yellow liquid (17.10 g, 79%; bp 38-42° C. at 0.8 mbar). MS (EI) 185.1 [M].

Step 6: 3-Methyl-4-trifluoromethyl-benzoic acid

A mixture of 3-methyl-4-trifluoromethyl-benzonitrile from step 5 (16.25 g, 88 mmol) and 3 N NaOH (88 mL, 264 mmol) in dioxane (90 mL) was refluxed for 18 h. The mixture was cooled to 23° C., diluted with TBME, acidified with 1 N HCl to pH 1 and extracted twice with TBME. The combined organic layers were washed with brine, dried over MgSO$_4$. Removal of the solvent in vacuum left the title compound as an off white solid (14.46 g, 81%), %), which was used without further purification. MS (ISN) 203.1 [M−H].

Step 7: N-Methoxy-3,N-dimethyl-4-trifluoromethyl-benzamide

To a suspension of 3-methyl-4-trifluoromethyl-benzoic acid from step 6 (14.1 g, 69.1 mmol), N,O-dimethylhydroxylamine hydrochloride (10.78 g, 111 mmol), N-methylmorpholine (12.14 mL, 111 mmol) and 4-DMAP (844 mg, 691 mmol) in DCM (230 mL) at 0° C. were added 1-(3-dimethylaminopropyl)-3-ethylcarbodiimide hydrochloride (EDC) (15.98 g, 82.9 mmol) and DMF (85 mL). The mixture was warmed up to 23° C. and was stirred for 18 h under nitrogen atmosphere. The mixture was diluted with TBME, washed with water and twice brine, dried over Na$_2$SO$_4$. Removal of the solvent in vacuum left the title compound as a brown oil (16.92 g, 99%), which was used without further purification. MS (ISP) 248.0 [M$^+$H].

Step 8: 1-(3-Methyl-4-trifluoromethyl-phenyl)-ethanone

To a solution of N-methoxy-3,N-dimethyl-4-trifluoromethyl-benzamide from step 7 (16.90 g, 68.36 mmol) in THF (280 mL) at −5° C. was added a 3 M methylmagnesium bromide solution in diethyl ether (45.6 mL, 136.7 mmol). The mixture was stirred at 0° C. for 1 h, then was warmed up to 23° C. and stirring was continued at 23° C. for further 1.5 h under nitrogen atmosphere. Then 1 N HCl (100 mL) was added drop wise to the mixture and stirring was continued for 30 min. The mixture was diluted with EtOAc and the aqueous layer was separated, the organic layer was washed with brine and dried over MgSO$_4$. Removal of the solvent in vacuum left the title compound as a light brown liquid (12.87 g, 93.1%), which was used without further purification. MS (EI) 202.1 [M].

Example A.5

3-Ethoxy-4-trifluoromethyl-acetophenone

The 1-(3-ethoxy-4-trifluoromethyl-phenyl)-ethanone was prepared by the following sequence:

Step 1: 5-Ethoxy-2-nitro-4-trifluoromethyl-phenylamine

To EtOH (500 mL) was added potassium metal (ca. 21 g, ca. 537 mmol) and the vigorous reaction had to be cooled with an ice bath. Stirring was continued until all potassium metal was dissolved. Solid commercially available 5-chloro-2-nitro-4-trifluoromethyl-phenylamine [CAS-No. 35375-74-7] (57.74 g, 240 mmol) was added in one portion and the resulting dark red mixture was stirred at 55-60° C. for 4 days. The warm reaction mixture was slowly poured into H$_2$O (ca. 2000 mL), adjusted pH with conc. HCl to pH 2, the yellow precipitate was filtered off, washed with H$_2$O and dried in air at 60° C. to give a yellow solid (57.81 g, 96%), which was used without further purification. MS (ISN) 249 [M$^-$H].

Step 2: 1-Bromo-5-ethoxy-2-nitro-4-trifluoromethyl-benzene

Solid 5-ethoxy-2-nitro-4-trifluoromethyl-phenylamine from step 1 (57.81 g, 231 mmol) was added slowly over 15 min to a rapidly stirred mixture of tert-butyl nitrite (45.8 mL, 347 mmol) and anhydrous copper(II) bromide (77.4 g, 347 mmol) in acetonitrile (462 mL), which was heated to 65° C. in an oil bath. Stirring at 65° C. was continued for 30 min, the reaction mixture was cooled to 23° C., poured into 1 N HCl, saturated with solid NaCl, extracted with TBME, dried over MgSO$_4$. Removal of the solvent in vacuum left a dark brown oil (74.5 g). Silica gel column chromatography with heptane/EtOAc 4:1 gave the title compound as a yellow solid (63.03 g, 87%). MS (EI) 313.0 [M] and 315.0 [M$^+$2].

Step 3: 5-Ethoxy-2-nitro-4-trifluoromethyl-benzonitrile

A mixture of 1-bromo-5-ethoxy-2-nitro-4-trifluoromethyl-benzene from step 2 (61.81 g, 197 mmol) and CuCN (18.51 g, 207 mmol) in NMP (197 mL) was heated to 150° C. for 30 min. Cooled to 23° C., poured into 1 N HCl, extracted with TBME, washed with brine, dried over Na$_2$SO$_4$. Removal of the solvent in vacuum left a brown oil. Silica gel column chromatography with heptane/EtOAc 4:1 gave the title compound as a yellow solid (46.73 g, 91%). MS (EI) 260.1 [M].

Step 4: 2-Amino-5-ethoxy-4-trifluoromethyl-benzonitrile

Iron powder (40.96 g, 733 mmol) was added in small portions over 5 min to a stirred suspension of finely grinded 5-ethoxy-2-nitro-4-trifluoromethyl-benzonitrile from step 3 (42.79 g, 164.5 mmol) in MeOH (85 mL) and conc. HCl (102 mL) with water bath cooling keeping the internal temperature at 40-50° C. The resulting mixture was stirred for further 1 h at ca. 50° C. and then poured into ice cold H$_2$O (700 mL). The precipitate was filtered, washed with water, dried, and dissolved in boiling EtOH (800 mL), activated carbon (ca. 10 g) was added, the mixture was refluxed for 45 min, the hot solution was filtered and evaporated to dryness to leave a yellow solid (31.81 g, 84%), which was used without further purification. MS (EI) 230.1 [M].

Step 5: 3-Ethoxy-4-trifluoromethyl-benzonitrile

To a solution of 2-amino-5-ethoxy-4-trifluoromethyl-benzonitrile from step 4 (31.62 g, 137.4 mmol) in dry THF (410 mL) was added isoamyl nitrite (40.4 mL, 302 mmol) and the mixture was refluxed for 16 h. The solvent was removed in vacuum to give an orange oil, which was dissolved in sat. NaHCO$_3$-sol., extracted three times with diethyl ether. The combined organic layers were washed with 1 N HCl and brine, dried over Na$_2$SO$_4$. Removal of the solvent in vacuum left an orange oil, which was purified by double Kugelrohr distillation (up to 160° C. bath temperature at 1.5 mbar) to give the title compound as a light yellow solid (25.06 g, 85%). MS (EI) 185.1 [M].

Step 6: 1-(3-Ethoxy-4-trifluoromethyl-phenyl)-ethanone

To a solution of 3-ethoxy-4-trifluoromethyl-benzonitrile from step 5 (5.00 g, 23.2 mmol), copper(I) bromide (100 mg, 0.7 mmol), tert.-butyldimethylchlorosilane (4.20 g, 27.9 mmol) in dry THF (30 mL) at −70° C. was drop wise added a 3 M methylmagnesium bromide solution in diethyl ether (13.2 mL, 39.6 mmol). The mixture was stirred at −70° C. for 10 min, then was warmed up to 0° C. and stirring was continued at 0° C. for further 2 h under nitrogen atmosphere. Poured the reaction mixture onto ice and sat. NH$_4$Cl-sol., extracted three times with diethyl ether, washed the combined organic layers with brine, dried over MgSO$_4$. Removal of the solvent in vacuum left a brown oil, which was purified by silica gel column chromatography with heptane/EtOAc 4:1 to give the title compound as a yellow liquid (1.84 g, 34%). MS (EI) 232 [M].

Example A.6

3-(2,2,2-Trifluoro-ethoxy)-4-trifluoromethyl-acetophenone

The 1-[3-(2,2,2-trifluoro-ethoxy)-4-trifluoromethyl-phenyl]-ethanone was prepared by the following sequence:

Step 1: 2-Nitro-5-(2,2,2-trifluoro-ethoxy)-4-trifluoromethyl-phenylamine

Commercially available 5-chloro-2-nitro-4-trifluoromethyl-phenylamine [CAS-No. 35375-74-7] (72.2 g, 300 mmol) was dissolved in DMSO (600 mL) and 2,2,2-trifluoroethanol (270 mL) were added at 23° C., the slightly exothermic reaction was cooled with a ice bath. KOH (85%, 99.0 g, 1500 mmol) were added slowly and the dark red reaction mixture was stirred at 23° C. for 4 days. Transferred into a 3 L flask and 1500 ml $H_2O$ were added under ice bath cooling, acidified with 3 N HCl and stirred at 23° C. for 3 h, filtered off the yellow precipitate, washed with $H_2O$ and dried in air at 60° C. to give the title compound as a yellow solid (89.47 g, 98%). MS (ISN) 303.1 [M−H].

Step 2: 1-Bromo-2-nitro-5-(2,2,2-trifluoro-ethoxy)-4-trifluoromethyl-benzene

Solid 2-nitro-5-(2,2,2-trifluoro-ethoxy)-4-trifluoromethyl-phenylamine from step 1 (24.28 g, 80 mmol) was added slowly over 15 min to a rapidly stirred mixture of tert-butyl nitrite (14.23 mL, 120 mmol) and anhydrous copper(II) bromide (26.75 g, 120 mmol) in acetonitrile (160 mL), which was heated to 65° C. in an oil bath. Stirring at 65° C. was continued for 2 h, the reaction mixture was cooled to 23° C., poured into 1 N HCl, saturated with solid NaCl, extracted with TBME, dried over $MgSO_4$. Removal of the solvent in vacuum left a dark brown oil (35.57 g). Silica gel column chromatography with heptane/EtOAc 4:1 gave the title compound as an orange solid (30.54 g, 104%), which was used without further purification. MS (EI) 367 [M] and 369 [M+2].

Step 3: 2-Nitro-5-(2,2,2-trifluoro-ethoxy)-4-trifluoromethyl-benzonitrile

A mixture of 1-bromo-2-nitro-5-(2,2,2-trifluoro-ethoxy)-4-trifluoromethyl-benzene from step 2 (30.54 g, 83.0 mmol) and CuCN (7.80 g, 87.1 mmol) in NMP (83 mL) was heated to 150° C. for 30 min. Cooled to 23° C., poured into 1 N HCl, extracted with EtOAc, washed with brine, dried over $Na_2SO_4$. Removal of the solvent in vacuum left a dark brown oil (33.9 g). Silica gel column chromatography with heptane/EtOAc 9:1->4:1 gave the title compound as a yellow solid (22.05 g, 85%). MS (EI) 314 [M].

Step 4: 2-Amino-5-(2,2,2-trifluoro-ethoxy)-4-trifluoromethyl-benzonitrile

Iron powder (15.80 g, 283.0 mmol) was added in small portions over 5 min to a stirred suspension of finely grinded 2-nitro-5-(2,2,2-trifluoro-ethoxy)-4-trifluoromethyl-benzonitrile from step 3 (19.93 g, 63.4 mmol) in MeOH (32 mL) and conc. HCl (40 mL) with water bath cooling keeping the internal temperature at 25-35° C. The resulting mixture was stirred for further 1 h at ca. 30° C. and then poured into ice cold $H_2O$ (400 mL). The precipitate was filtered, washed with water, dried, and dissolved in boiling EtOH (400 mL), activated carbon (ca. 10 g) was added, the mixture was refluxed for 45 min, the hot solution was filtered and evaporated to dryness to leave a dark green solid (15.96 g, 84%), which was further purified by silica gel column chromatography with heptane/EtOAc 4:1 to give the title compound as a yellow solid (14.56 g, 81%). MS (ISN) 283 [M−H].

Step 5: 3-(2,2,2-Trifluoro-ethoxy)-4-trifluoromethyl-benzonitrile

To a solution of 2-amino-5-(2,2,2-trifluoro-ethoxy)-4-trifluoromethyl-benzonitrile from step 4 (14.47 g, 50.9 mmol) in dry THF (153 mL) was added isoamyl nitrite (15.0 mL, 112.0 mmol) and the mixture was refluxed for 20 h. The solvent was removed in vacuum to give an orange oil, which was dissolved in TBME, washed with 1 N HCl, sat. $NaHCO_3$-sol. and brine, dried over $Na_2SO_4$. Removal of the solvent in vacuum left a brown solid (15.05 g), which was purified by Kugelrohr distillation (up to 155° C. bath temperature at 1.2 mbar) to give the title compound as a light yellow solid (10.83 g, 79%). MS (EI) 269 [M].

Step 6: 3-(2,2,2-Trifluoro-ethoxy)-4-trifluoromethyl-benzoic acid

A mixture of 3-(2,2,2-trifluoro-ethoxy)-4-trifluoromethyl-benzonitrile from step 5 (8.75 g, 33 mmol) and 3 M NaOH (3.9 g, 98 mmol in 33 mL H2O) in dioxane (33 mL) was refluxed for 7.5 h. Poured onto ice, acidified with conc. HCl to pH 1, saturated with solid NaCl, extracted with TBME, dried over $MgSO_4$. Removal of the solvent in vacuum left the title compound as an off-white solid (9.22 g, 98%), %), which was used without further purification. MS (ISN) 286.9 [M–H].

Step 7: N-Methoxy-N-methyl-3-(2,2,2-trifluoro-ethoxy)-4-trifluoromethyl-benzamide To a mixture of 3-(2,2,2-trifluoro-ethoxy)-4-trifluoromethyl-benzoic acid from step 6 (9.22 g, 32 mmol), N,O-dimethylhydroxylamine hydrochloride (5.00 g, 51 mmol), N-methylmorpholine (5.62 mL, 51 mmol) and 4-DMAP (391 mg, 3.2 mmol) in DCM (100 mL) and DMF (20 mL) at 0° C. was added 1-(3-dimethylaminopropyl)-3-ethylcarbodiimide hydrochloride (EDC) (7.36 g, 38 mmol) and the mixture was stirred at 23° C. for 18 h. Poured onto ice cold 1 N HCl, extracted with TBME, washed with sat. $NaHCO_3$-sol. and brine, dried over $Na_2SO_4$. Removal of the solvent in vacuum left the title compound as a brown oil (10.555 g, 100%), %), which was used without further purification. MS (EI) 331.0 [M].

Step 8: 1-[3-(2,2,2-Trifluoro-ethoxy)-4-trifluoromethyl-phenyl]-ethanone

To a solution of N-methoxy-N-methyl-3-(2,2,2-trifluoro-ethoxy)-4-trifluoromethyl-benzamide from step 7 (10.467 g, 32 mmol) in THF (100 mL) at −5° C. was added methylmagnesium bromide (3 M in $Et_2O$, 21.1 mL, 64 mmol). The mixture was stirred at 0° C. for 15 min, then warmed up to 23° C., stirring was continued for further 1.5 h at 23° C. Cooled to 0° C., 1 N HCl (150 mL) was added dropwise, stirring was continued at 23° C. for 15 min, the mixture was diluted with TBME, the phases were separated, the organic layer was washed with water and brine, dried over MgSO4. Removal of the solvent in vacuum left a yellow solid (9.021 g, 100%), which was used without further purification. MS (EI) 286.1 [M].

B—Amide Derivatives of Formula (VII)

Example B.1

4-Amino-5-chloro-thiophene-2-sulfonic acid amide

Hydrogenation of a stirred solution of 5-chloro-4-nitro-thiophene-2-sulfonamide [CAS-No. 61714-46-3; commercially available] (1.13 g, 4.66 mmol) in methanol (140 ml) on Raney-Nickel (1.13 g) for 3 h at room temperature yielded after removal of the catalyst by filtration, evaporation and column chromatography on silica gel (ethyl acetate/hexane) the title compound as a light brown solid. MS (ISP) 211.0 [(M−H)⁻], mp 138° C.

Example B.2

4-Amino-5-chloro-thiophene-2-sulfonic acid (2-hydroxy-1,1-dimethyl-ethyl)-amide a) To a stirred solution of 2-amino-2-methyl-1-propanol (0.75 g, 8.39 mmol) in dioxane (21 ml) was added at room temperature 5-chloro-4-nitrothiophene-2-sulfonyl chloride (2.0 g, 7.63 mmol) and triethylamine (1.17 ml, 8.39 mmol). The light yellow suspension was stirred at room temperature for 17 h, poured into water (100 ml) and extracted with dichloromethane (3×75 ml). The combined organic layers were washed with water (100 ml) and brine (70 ml), dried (MgSO₄) and evaporated. The crude product was further purified by column chromatography on silica gel (heptane/ethyl acetate 1:1) and subsequent crystallization from ethyl acetate/hexane to yield 5-chloro-4-nitro-thiophene-2-sulfonic acid (2-hydroxy-1,1-dimethyl-ethyl)-amide (0.73 g, 30%) as a light brown solid. MS (ISP) 313.1 [(M−H)⁻], mp 136° C.

b) Hydrogenation of a stirred solution of 5-chloro-4-nitrothiophene-2-sulfonic acid (2-hydroxy-1,1-dimethyl-ethyl)-amide (0.66 g, 2.1 mmol) in methanol (70 ml) on Raney-Nickel (0.66 g) for 3 h at room temperature yielded after removal of the catalyst by filtration, evaporation and purification of the crude product by column chromatography on silica gel (ethyl acetate/hexane) followed by crystallization from ethyl acetate/hexane the title compound (0.41 g, 69%) as a light brown solid. MS (ISP) 282.8 [(M−H)⁻], mp 113° C.

Example B.3

2-Amino-4-methyl-thiazole-5-sulfonic acid (2-hydroxy-1,1-dimethyl-ethyl)-amide a) To a stirred solution of 2-amino-2-methyl-1-propanol (1.14 g, 13 mmol) in dioxane (20 ml) was added at 0° C. (ice water bath) commercially available 2-acetamido-4-methylthiazole-5-sulfonyl chloride (2.95 g, 12 mmol) and triethylamine (1.78 ml, 13 mmol). The light yellow suspension was stirred at room temperature for 17 h, poured into water (100 ml) and extracted with dichloromethane (2×10 ml). The combined organic layers were washed with sat. NaHCO₃ solution (2×70 ml) and brine (70 ml), dried (MgSO₄) and evaporated. The crude product was further purified by column chromatography on silica gel (ethyl acetate/MeOH 9:1) and subsequent crystallization (ethyl acetate/MeOH/heptane) to yield 2-acetamido-4-methyl-thiazole-5-sulfonic acid (2-hydroxy-1,1-dimethyl-ethyl)-amide (1.15 g, 32%) as a light brown solid. MS (ISP) 306.1 [(M−H)⁻]; mp 194° C.

b) A stirred suspension of 2-acetamido-4-methyl-thiazole-5-sulfonic acid (2-hydroxy-1,1-dimethyl-ethyl)-amide (1.15 g, 3.58 mmol) in 6N hydrochloric acid (14 ml) was heated for 2 h at 80° C., evaporated., and saturated NaHCO₃ solution (30 ml) was added. The mixture was extracted with ethyl acetate (3×50 ml), the combined organic layers washed with brine (30 ml), dried (MgSO₄) and evaporated. The crude product was further purified by column chromatography on silica gel (dichloromethane/MeOH/NH₄OH 80:10:1) to yield the title compound (0.68 g, 71%) as a white solid. MS (ISP) 264.0 [(M−H)⁻]; mp 146° C.

Example B.4

4-Amino-5-chloro-thiophene-2-sulfonic acid (2-hydroxy-1-hydroxymethyl-ethyl)-amide a) To a stirred solution of 2-amino-1,3-propanediol (0.5 g, 5.49 mmol) in water (2 ml) was added at room temperature magnesium oxide (1.11 g, 27.5 mmol) and THF (6 ml). The suspension was stirred at room temperature for 30 min and a solution of 5-chloro-4-nitrothiophene-2-sulfonyl chloride (2.88 g, 10.9 mmol) in THF (2 ml) was added. The light yellow suspension was stirred at room temperature for 1 h and, after filtration on Dicalit, evaporated. Water (60 ml) was added and the mixture was extracted with ethyl acetate (3×50 ml). The combined organic layers were washed with brine (70 ml), dried (MgSO₄) and evaporated. The crude product was further purified by column chromatography on silica gel (heptane/ethyl acetate 1:1) and subsequent crystallization from ethyl acetate/hexane to yield 5-chloro-4-nitro-thiophene-2-sulfonic acid (2-hydroxy-1-hydroxymethyl-ethyl)-amide (0.76 g, 44%) as a light yellow solid. MS (ISP) 314.9 [(M−H)⁻], mp 142° C.

b) Hydrogenation of a stirred solution of 5-chloro-4-nitrothiophene-2-sulfonic acid (2-hydroxy-1-hydroxymethyl-ethyl)-amide (0.67 g, 2.12 mmol) in methanol (67 ml) on Raney-Nickel (0.67 g) for 2.5 h at room temperature yielded after removal of the catalyst by filtration, evaporation and purification of the crude product by column chromatography on silica gel (dichloromethane/MeOH) followed by crystallization from ethyl acetate/hexane the title compound (0.47 g, 77%) as a light brown solid. MS (ISP) 286.8 [(M+H)⁺], mp 132° C.

Example B.5

4-Amino-5-chloro-thiophene-2-sulfonic acid bis-(2-hydroxy-ethyl)-amide a) To a stirred solution of diethanolamine (1.16 g, 11 mmol) in water (4 ml) was added at room temperature magnesium oxide (2.22 g, 55 mmol) and THF (16 ml). The suspension was stirred at room temperature for 30 min and a solution of 5-chloro-4-nitrothiophene-2-sulfonyl chloride (3.46 g, 13.2 mmol) in THF (4 ml) was added. The light yellow suspension was stirred at room temperature for 1 h and, after filtration on Dicalit, evaporated. Water (60 ml) was added and the mixture was extracted with ethyl acetate (3×50 ml). The combined organic layers were washed with brine (70 ml), dried (MgSO₄) and evaporated. The crude product was further purified by flash chromatography on silica gel (heptane/ethyl acetate) to yield 5-chloro-4-nitro-thiophene-2-sulfonic acid bis-(2-hydroxy-ethyl)-amide (0.48 g, 13%) as a yellow solid. MS (ISP) 331.2 [(M+H)⁺], mp 113° C.

b) Hydrogenation of a stirred solution of 5-chloro-4-nitrothiophene-2-sulfonic acid bis-(2-hydroxy-ethyl)-amide (0.40 g, 1.21 mmol) in methanol (40 ml) on Raney-Nickel (0.40 g) for 4 h at room temperature yielded after removal of the catalyst by filtration, evaporation and purification of the crude product by flash chromatography on silica gel (dichloromethane/MeOH) the title compound (0.19 g, 52%) as a yellow solid. MS (ISP) 301.0 [(M+H)⁺], mp 96° C.

Example B.6

4-Amino-5-chloro-thiophene-2-sulfonic acid (2-hydroxy-ethyl)-amide a) To a stirred solution of ethanolamine (0.67 g, 11 mmol) in water (4 ml) was added at room temperature magnesium oxide (2.22 g, 55 mmol) and THF (12 ml). The suspension was stirred at room temperature for 30 min and a solution of 5-chloro-4-nitrothiophene-2-sulfonyl chloride (3.46 g, 13.2 mmol) in THF (4 ml) was added. The light yellow suspension was stirred at room temperature for 1 h and, after filtration on Dicalit, evaporated. Water (60 ml) was added and the mixture was extracted with ethyl acetate (3×50 ml). The combined organic layers were washed with brine (70 ml), dried ($MgSO_4$) and evaporated. The crude product was further purified by flash chromatography on silica gel (heptane/ethyl acetate) and subsequent crystallization from ethyl acetate/hexane to yield 5-chloro-4-nitro-thiophene-2-sulfonic acid (2-hydroxy-ethyl)-amide (1.39 g, 44%) as a yellow solid. MS (ISP) 284.8 [(M−H)⁻], mp 99° C.

b) Hydrogenation of a stirred solution of 5-chloro-4-nitrothiophene-2-sulfonic acid bis-(2-hydroxy-ethyl)-amide (1.28 g, 4.46 mmol) in methanol (120 ml) on Raney-Nickel (1.28 g) for 4 h at room temperature yielded after removal of the catalyst by filtration, evaporation and purification of the crude product by flash chromatography on silica gel (dichloromethane/MeOH) the title compound (0.78 g, 68%) as a yellow solid. MS (ISP) 254.9 [(M−H)⁻], mp 100° C.

Example B.7

4-Amino-5-chloro-thiophene-2-sulfonic acid (2-hydroxy-1-hydroxymethyl-1-methyl-ethyl)-amide a) To a stirred solution of 2-amino-2-methyl-1,3-propanediol (0.44 g, 4.2 mmol) in THF (10 ml) was added at room temperature 5-chloro-4-nitrothiophene-2-sulfonyl chloride (1.0 g, 3.82 mmol) and triethylamine (0.58 ml, 4.2 mmol). The light yellow suspension was stirred at room temperature for 17 h, poured into water (100 ml) and extracted with dichloromethane (3×75 ml). The combined organic layers were washed with water (100 ml) and brine (70 ml), dried ($MgSO_4$) and evaporated. The crude product was further purified by flash chromatography on silica gel (heptane/ethyl acetate) and subsequent crystallization from ethyl acetate/hexane to yield 5-chloro-4-nitro-thiophene-2-sulfonic acid (2-hydroxy-1-hydroxymethyl-1-methyl-ethyl)-amide (0.25 g, 20%) as a light brown solid. Mp 133° C.

b) Hydrogenation of a stirred solution of 5-chloro-4-nitrothiophene-2-sulfonic acid (2-hydroxy-1-hydroxymethyl-1-methyl-ethyl)-amide (0.25 g, 0.76 mmol) in methanol (30 ml) on Raney-Nickel (0.26 g) for 5 h at room temperature yielded after removal of the catalyst by filtration, evaporation and purification of the crude product by flash chromatography on silica gel (ethyl acetate/heptane) followed by crystallization from ethyl acetate/hexane the title compound (0.16 g, 68%) as a light brown solid. MS (ISP) 299.1 [(M−H)⁻], mp 136° C.

Example B.8

2-Amino-4-methyl-thiazole-5-sulfonic acid bis-(2-hydroxy-ethyl)-amide a) To a stirred solution of diethanolamine (1.24 g, 11.8 mmol) in dioxane (20 ml) was added at 0° C. (ice water bath) commercially available 2-acetamido-4-methyl-thiazole-5-sulfonyl chloride (1.0 g, 3.93 mmol) and triethylamine (0.6 ml, 4.32 mmol). The light yellow suspension was stirred at room temperature for 17 h, and evaporated. The crude product was further purified by flash chromatography on silica gel (dichloromethane/MeOH) and subsequent crystallization (dichloromethane/MeOH/hexane) to yield 2-acetamido-4-methyl-thiazole-5-sulfonic acid bis-(2-hydroxyethyl)-amide (0.74 g, 58%) as a white solid. MS (ISP) 324.0 [(M+H)⁺]; mp 204° C.

b) A stirred suspension of 2-acetamido-4-methyl-thiazole-5-sulfonic acid bis-(2-hydroxy-ethyl)-amide (0.7 g, 2.16 mmol) in 6N hydrochloric acid (8 ml) was heated for 2 h at 80° C., evaporated., and saturated $NaHCO_3$ solution (50 ml) was added. The mixture was extracted with ethyl acetate (3×50 ml), the combined organic layers washed with brine (30 ml) and dried ($MgSO_4$). The crude product was further purified by crystallization (hexane) to yield the title compound (0.45 g, 74%) as a white solid. MS (ISP) 281.9 [(M+H)⁺]; mp 141° C.

Example B.9

2-Amino-4-methyl-thiazole-5-sulfonic acid (2-hydroxy-1-hydroxymethyl-1-methyl-ethyl)-amide a) To a stirred solution of 2-amino-2-methyl-1,3-propanediol (1.86 g, 17.7 mmol) in dioxane (20 ml) was added at 0° C. (ice water bath) commercially available 2-acetamido-4-methylthiazole-5-sulfonyl chloride (1.5 g, 5.89 mmol) and triethylamine (0.9 ml, 6 mmol). The light yellow suspension was stirred at room temperature for 17 h, and evaporated. The crude product was further purified by flash chromatography on silica gel (ethyl acetate/MeOH) and subsequent crystallization (dichloromethane/MeOH/hexane) to yield 2-acetamido-4-methylthiazole-5-sulfonic acid (2-hydroxy-1-hydroxymethyl-1-methyl-ethyl)-amide (0.33 g, 17%) as a white solid. MS (ISP) 322.2 [(M−H)⁻]; mp 201° C.

b) A stirred suspension of 2-acetamido-4-methyl-thiazole-5-sulfonic acid (2-hydroxy-1-hydroxymethyl-1-methylethyl)-amide (0.33 g, 1.02 mmol) in 6N hydrochloric acid (4 ml) was heated for 2 h at 80° C., evaporated., and saturated $NaHCO_3$ solution (30 ml) was added. The mixture was extracted with ethyl acetate (3×50 ml), the combined organic layers washed with brine (30 ml) and dried ($MgSO_4$). The crude product was further purified by crystallization (dichloromethane/MeOH/hexane) to yield the title compound (0.11 g, 38%) as a white solid. MS (ISP) 280.0 [(M−H)⁻]; mp 170° C.

Example B.10

2-Amino-4-methyl-thiazole-5-sulfonic acid (2-hydroxy-ethyl)-amide a) To a stirred solution of ethanolamine (1.08 g, 17.7 mmol) in dioxane (20 ml) was added at 0° C. (ice water bath) commercially available 2-acetamido-4-methylthiazole-5-sulfonyl chloride (1.5 g, 5.89 mmol) and triethylamine (0.9 ml, 6 mmol). The light yellow suspension was stirred at room temperature for 17 h, and evaporated. The crude product was further purified by flash chromatography on silica gel (ethyl acetate/MeOH) and subsequent crystallization (dichloromethane/MeOH/hexane) to yield 2-acetamido-4-methyl-thiazole-5-sulfonic acid (2-hydroxy-ethyl)-amide (1.0 g, 61%) as a white solid. MS (ISP) 278.0 [(M−H)⁻]; mp 211° C.

b) A stirred suspension of 2-acetamido-4-methyl-thiazole-5-sulfonic acid (2-hydroxy-ethyl)-amide (0.95 g, 3.4 mmol) in 6N hydrochloric acid (13 ml) was heated for 2 h at 80° C., evaporated, and saturated NaHCO$_3$ solution (20 ml) was added. The mixture was extracted with ethyl acetate (3×50 ml), the combined organic layers washed with brine (50 ml) and dried (MgSO$_4$). The crude product was further purified by crystallization (dichloromethane/MeOH/hexane) to yield the title compound (0.51 g, 63%) as a white solid. MS (ISP) 236.0 [(M–H)$^-$]; mp 151° C.

Example B.11

4-Amino-5-methyl-thiophene-2-sulfonic acid amide a) To a stirred solution of 5-methyl-4-nitrothiophene-2-sulfonyl chloride [CAS No. 61714-77-0] (1.0 g, 4.14 mmol) in THF (20 ml) was added at 0° C. (ice water bath) ammonium hydroxide solution (25%, 5 ml). The reaction mixture was stirred at room temperature for 1 h, evaporated, poured into water (30 ml) and extracted with ethyl acetate (2×50 ml). The combined organic layers were washed with brine (2×30 ml), dried (MgSO$_4$) and evaporated. The crude product was further purified by crystallization from ethyl acetate/hexane to yield 5-methyl-4-nitro-thiophene-2-sulfonamide (0.75 g, 82%) as a brown solid. MS (ISP) 221.0 [(M–H)$^-$], mp 120° C.

b) Hydrogenation of a stirred solution of 5-methyl-4-nitro-thiophene-2-sulfonamide (0.50 g, 2.25 mmol) in methanol (15 ml) on Raney-Nickel (0.5 g) for 16 h at room temperature yielded after removal of the catalyst by filtration, evaporation and crystallization (methanol/diethyl ether/hexane) the title compound as a light brown solid. MS (ISP) 191.0 [(M–H)$^-$], mp 175° C.

Example B.12

4-Amino-5-methyl-thiophene-2-sulfonic acid (2-hydroxy-1,1-dimethyl-ethyl)-amide a) To a stirred solution of 2-amino-2-methyl-1-propanol (1.11 g, 12.4 mmol) in dioxane (20 ml) was added at 0° C. (ice water bath) 5-methyl-4-nitrothiophene-2-sulfonyl chloride [CAS No. 61714-77-0] and triethylamine (0.63 ml, 4.56 mmol). The light yellow suspension was stirred at room temperature for 17 h, and evaporated. The crude product was further purified by column chromatography on silica gel (ethyl acetate/MeOH) and subsequent crystallization (ethyl acetate/heptane) to yield 5-methyl-4-nitro-thiophene-2-sulfonic acid (2-hydroxy-1,1-dimethyl-ethyl)-amide (0.71 g, 58%) as a light brown solid. MS (ISP) 293.0 [(M–H)$^-$]; mp 126° C.

b) Hydrogenation of a stirred solution of 5-methyl-4-nitro-thiophene-2-sulfonic acid (2-hydroxy-1,1-dimethyl-ethyl)-amide (0.60 g, 2.04 mmol) in methanol (20 ml) on Raney-Nickel (0.6 g) for 7 h at room temperature yielded after removal of the catalyst by filtration, evaporation and crystallization (diethyl ether/hexane) the title compound as an off-white solid. MS (ISP) 262.9 [(M–H)$^-$], mp 118° C.

Example B.13

2-Amino-thiazole-5-sulfonic acid (2-hydroxy-1,1-dimethyl-ethyl)-amide a) To a stirred solution of 2-amino-2-methyl-1-propanol (1.11 g, 12.5 mmol) in dioxane (20 ml) was added at 0° C. (ice water bath) 2-acetamido-thiazole-5-sulfonyl chloride [CAS No. 69812-30-2; commercially available] (1.0 g, 4.15 mmol) and triethylamine (0.64 ml, 4.57 mmol). The light yellow suspension was stirred at room temperature for 17 h, and evaporated. The crude product was further purified by column chromatography on silica gel (ethyl acetate) to yield 2-acetamido-thiazole-5-sulfonic acid (2-hydroxy-1,1-dimethyl-ethyl)-amide (0.72 g, 59%) as a white solid. MS (ISP) 292.1 [(M–H)$^-$]; mp 206° C.

b) A stirred suspension of 2-acetamido-thiazole-5-sulfonic acid (2-hydroxy-1,1-dimethyl-ethyl)-amide (0.68 g, 2.32 mmol) in 6N hydrochloric acid (20 ml) was heated for 2 h at 80° C., evaporated., and saturated NaHCO$_3$ solution (30 ml) was added. The mixture was extracted with ethyl acetate (3×50 ml), the combined organic layers washed with brine (30 ml), dried (MgSO$_4$) and evaporated. The crude product was further purified by column chromatography on silica gel (dichloromethane/MeOH/NH$_4$OH 80:10:1) to yield the title compound (0.42 g, 72%) as a colorless oil. MS (ISP) 250.0 [(M–H)$^-$].

Example B.14

4-Amino-5-chloro-thiophene-2-sulfonic acid (2-dimethylamino-ethyl)-amide a) To a stirred solution of N,N-dimethylethylenediamine (0.67 g, 7.6 mmol) in dioxane (25 ml) was added at room temperature 5-chloro-4-nitrothiophene-2-sulfonyl chloride (2.0 g, 7.64 mmol) and triethylamine (1.17 ml, 8.4 mmol). The light yellow suspension was stirred at room temperature for 17 h, and evaporated. The crude product was further purified by flash chromatography on silica gel (dichloromethane/methanol), and subsequent crystallization from ethyl acetate to yield 5-chloro-4-nitro-thiophene-2-sulfonic acid (2-dimethylamino-ethyl)-amide (1.16 g, 48%) as a light brown solid. MS (ISP) 312.0 [(M–H)$^-$], mp 178° C.

b) Hydrogenation of a stirred solution of 5-chloro-4-nitro-thiophene-2-sulfonic acid bis-(2-dimethylamino-ethyl)-amide (1.09 g, 3.47 mmol) in methanol (100 ml) and tetrahydrofurane (30 ml) on Raney-Nickel (1.1 g) for 5 h at room temperature yielded after removal of the catalyst by filtration, evaporation and purification of the crude product by crystallization (ethyl acetate/MeOH) the title compound (0.64 g, 65%) as a brown solid. MS (ISP) 282.0 [(M–H)$^-$], mp 184° C.

Example B.15

2-Amino-4-methyl-thiazole-5-sulfonic acid (2-dimethylamino-ethyl)-amide a) To a stirred solution of N,N-dimethylethylenediamine (1.04 g, 11.8 mmol) in tetrahydrofurane (14 ml) was added at 0° C. (ice water bath) commercially available 2-acetamido-4-methylthiazole-5-sulfonyl chloride (1.0 g, 3.93 mmol) and triethylamine (0.6 ml, 4 mmol). The light yellow suspension was stirred at room temperature for 17 h, and evaporated. The crude product was further purified by column chromatography on silica gel (dichloromethane/MeOH/NH$_4$OH 80:10:1) and subsequent crystallization (dichloromethane/hexane) to yield 2-acetamido-4-methyl-thiazole-5-sulfonic acid (2-dimethylamino-ethyl)-amide (1.07 g, 89%) as a white solid. MS (ISP) 305.1 [(M–H)$^-$]; mp 143° C.

b) A stirred suspension of 2-acetamido-4-methyl-thiazole-5-sulfonic acid (2-dimethylamino-ethyl)-amide (1.0 g, 3.26 mmol) in 6N hydrochloric acid (13 ml) was heated for 2 h at 80° C., and 2N NaHCO$_3$ solution (100 ml) was added. The mixture was extracted with ethyl acetate (3×50 ml), the combined organic layers washed with brine (50 ml) and dried (MgSO$_4$). The crude product was further purified by crystallization (ethyl aceate) to yield the title compound (0.68 g, 79%) as a white solid. MS (ISP) 262.9 [(M−H)$^-$]; mp 153° C.

Example B.16

2-Amino-4-methyl-thiazole-5-sulfonic acid (2-hydroxy-1-hydroxymethyl-ethyl)-amide a) To a stirred solution of 2-amino-1,3-propanediol (2.15 g, 23.6 mmol) in THF (26 ml) was added at 0° C. (ice water bath) commercially available 2-acetamido-4-methylthiazole-5-sulfonyl chloride (2.0 g, 7.85 mmol) and triethylamine (1.2 ml, 8.64 mmol). The light yellow suspension was stirred at room temperature for 17 h, and evaporated. The crude product was further purified by column chromatography on silica gel (dichloromethane/MeOH/NH$_4$OH 80:10:1) to yield 2-acetamido-4-methyl-thiazole-5-sulfonic acid (2-hydroxy-1-hydroxymethyl-ethyl)-amide (1.46 g, 60%) as a light yellow solid. MS (ISP) 308.1 [(M−H)$^-$]; mp 217° C.

b) A stirred suspension of 2-acetamido-4-methyl-thiazole-5-sulfonic acid (2-hydroxy-1-hydroxymethyl-ethyl)-amide (1.45 g, 4.69 mmol) in 6N hydrochloric acid (22 ml) was heated for 2 h at 80° C., evaporated, and saturated NaHCO$_3$ solution (50 ml) was added. The mixture was extracted with ethyl acetate (3×50 ml), the combined organic layers washed with brine (50 ml), dried (MgSO$_4$) and evaporated. The crude product was further purified by crystallization (dichloromethane/MeOH/hexane) to yield the title compound (0.55 g, 44%) as an off-white solid. MS (ISP) 266.0 [(M−H)$^-$].

Example B.17

[2-(4-Amino-5-chloro-thiophene-2-sulfonylamino)-ethyl]-carbamic acid tert-butyl ester a) To a stirred solution of tert-butyl N-(2-aminoethyl)-carbamate (0.46 g, 2.87 mmol) in THF (6 ml) was added at 0° C. (ice water bath) 5-chloro-4-nitrothiophene-2-sulfonyl chloride (0.5 g, 1.91 mmol) and triethylamine (0.29 ml, 2.1 mmol). The light yellow suspension was stirred at room temperature for 17 h, and evaporated. The crude product was further purified by flash chromatography on silica gel (ethyl acetate/heptane), and subsequent crystallization from ethyl acetate/hexane to yield [2-(5-chloro-4-nitro-thiophene-2-sulfonylamino)-ethyl]-carbamic acid tert-butyl ester (0.53 g, 72%) as a light yellow solid. MS (ISP) 384.1 [(M−H)$^-$], mp 147° C.

b) Hydrogenation of a stirred solution of [2-(5-chloro-4-nitro-thiophene-2-sulfonylamino)-ethyl]-carbamic acid tert-butyl ester (0.47 g, 1.22 mmol) in methanol (40 ml) on Raney-Nickel (0.47 g) for 5 h at room temperature yielded after removal of the catalyst by filtration, evaporation and purification of the crude product by crystallization (dichloromethane/MeOH) the title compound (0.38 g, 88%) as a light brown solid. MS (ISP) 354.1 [(M−H)$^-$], mp 116° C.

Example B.18

(RS)-1-(4-Amino-5-chloro-thiophene-2-sulfonyl)-pyrrolidin-3-ol a) To a stirred solution of (RS)-3-pyrrolidinol (0.75 g, 8.6 mmol) in THF (18 ml) was added at room temperature 5-chloro-4-nitrothiophene-2-sulfonyl chloride (1.5 g, 5.72 mmol) and triethylamine (0.88 ml, 6.3 mmol). The light yellow suspension was stirred at room temperature for 17 h, and evaporated. The crude product was further purified by column chromatography on silica gel (ethyl acetate), and subsequent crystallization from dichloromethane/MeOH/hexane to yield (RS)-1-(5-chloro-4-nitro-thiophene-2-sulfonyl)-pyrrolidin-3-ol (0.65 g, 36%) as a yellow solid. MS (EI) 312.0 [(M)$^+$], mp 96° C.

b) Hydrogenation of a stirred solution of (RS)-1-(5-chloro-4-nitro-thiophene-2-sulfonyl)-pyrrolidin-3-ol (0.92 g, 2.94 mmol) in methanol (90 ml) on Raney-Nickel (0.92 g) for 7 h at room temperature yielded after removal of the catalyst by filtration, evaporation and purification of the crude product by flash chromatography (ethyl acetate/heptane) and subsequent crystallization (dichloromethane/MeOH/hexane) the title compound (0.30 g, 36%) as a yellow solid. MS (EI) 282.0 [(M)$^+$], mp 156° C.

Example B.19

4-Methyl-5-(4-methyl-piperazine-1-sulfonyl)-thiazol-2-ylamine a) To a stirred solution of 1-methylpiperazine (1.18 g, 11.8 mmol) in THF (24 ml) was added at 0° C. (ice water bath) commercially available 2-acetamido-4-methylthiazole-5-sulfonyl chloride (2.0 g, 7.85 mmol) and triethylamine (1.2 ml, 8.6 mmol). The light yellow suspension was stirred at room temperature for 17 h, and evaporated. The crude product was further purified by column chromatography on silica gel (dichloromethane/MeOH 9:1) and subsequent crystallization (dichloromethane/MeOH/hexane) to yield 2-acetamido-4-methyl-thiazole-5-sulfonic acid (4-methylpiperazinyl)-amide (1.85 g, 74%) as a white solid. MS (ISP) 319.0 [(M+H)$^+$]; mp 245° C.

b) A stirred suspension of 2-acetamido-4-methyl-thiazole-5-sulfonic acid (4-methylpiperazinyl)-amide (1.73 g, 5.43 mmol) in 6N hydrochloric acid (22 ml) was heated for 2 h at 80° C., evaporated, and saturated NaHCO$_3$ solution (75 ml) was added. The mixture was extracted with ethyl acetate (3×50 ml), the combined organic layers washed with brine (50 ml), dried (MgSO$_4$) and evapoarted. The crude product was further purified by crystallization (ethyl acetate/MeOH/hexane) to yield the title compound (1.14 g, 76%) as a white solid. MS (ISP) 277.0 [(M+H)$^+$]; mp 188° C.

Example B.20

2-Amino-4-methyl-thiazole-5-sulfonic acid (2-hydroxy-ethyl)-methyl-amide a) To a stirred solution of 2-(methylamino)-ethanol (0.44 g, 5.86 mmol) in THF (12 ml) was added at 0° C. (ice water bath) commercially available 2-acetamido-4-methylthiazole-5-sulfonyl chloride (1.0 g, 3.92 mmol) and triethylamine (0.6 ml, 4.32 mmol). The light yellow suspension was stirred at room temperature for 17 h, and evaporated. The crude product was further purified by flash chromatography on silica gel (dichloromethane/MeOH) and subsequent crystallization (dichloromethane/MeOH/hexane) to yield 2-acetamido-4-methyl-thiazole-5-sulfonic acid (2-hydroxy-ethyl)-methyl-amide (0.93 g, 81%) as a white solid. MS (ISP) 294.0 [(M+H)+]; mp 189° C.

b) A stirred suspension of 2-acetamido-4-methyl-thiazole-5-sulfonic acid (2-hydroxy-ethyl)-methyl-amide (0.85 g, 2.9 mmol) in 6N hydrochloric acid (13 ml) was heated for 2 h at 80° C., evaporated, and saturated NaHCO$_3$ solution (50 ml) was added. The mixture was extracted with ethyl acetate (3×50 ml), the combined organic layers washed with brine (50 ml), dried (MgSO$_4$) and evaporated. The crude product was further purified by crystallization (dichloromethane/MeOH/hexane) to yield the title compound (0.49 g, 67%) as a white solid. MS (EI) 251.1 [(M)+]; mp 118° C.

Example B.21

4-Amino-5-chloro-thiophene-2-sulfonic acid (2-hydroxy-ethyl)-methyl-amide a) A suspension of 2-(methylamino)-ethanol (0.29 g, 3.86 mmol) and magnesium oxide (0.77 g, 19.1 mmol) in THF (4 ml) and water (1.4 ml) was allowed to stir at room temperature for 30 min, 5-chloro-4-nitrothiophene-2-sulfonyl chloride (1.0 g, 3.81 mmol) dissolved in THF (1.6 ml) was added drop wise at room temperature over a period of 1 h and the reaction mixture was allowed to stir for an additional hour. Filtration over Decalite and evaporation yielded the crude product which was further purified by flash chromatography on silica gel (ethyl acetate/heptane) to yield 5-chloro-4-nitro-thiophene-2-sulfonic acid (2-hydroxy-ethyl)-methyl-amide (0.4 g, 35%) as a yellow solid. MS (EI) 300.0 [(M)+], mp 62° C.

b) Hydrogenation of a stirred solution of 5-chloro-4-nitro-thiophene-2-sulfonic acid (2-hydroxy-ethyl)-methyl-amide (0.58 g, 1.93 mmol) in methanol (50 ml) on Raney-Nickel (0.58 g) for 6 h at room temperature yielded after removal of the catalyst by filtration, evaporation and purification of the crude product by flash chromatography (dichloromethane/MeOH) the title compound (0.15 g, 29%) as a yellow oil. MS (ISP) 270.9 [(M+H)+].

Example B.22

2-Chloro-5-(4-methyl-piperazine-1-sulfonyl)-thiophen-3-ylamine a) A suspension of 1-methyl-piperazine (0.38 g, 3.79 mmol) and magnesium oxide (0.38 g, 9.43 mmol) in THF (2.1 ml) and water (0.7 ml) was allowed to stir at room temperature for 30 min, 5-chloro-4-nitrothiophene-2-sulfonyl chloride (0.5 g, 1.91 mmol) dissolved in THF (0.7 ml) was added drop wise at room temperature over a period of 1 h and the reaction mixture was allowed to stir for an additional hour. Filtration over Decalite and evaporation yielded the crude product which was further purified by flash chromatography on silica gel (dichloromethane/MeOH) to yield 5-chloro-4-nitro-thiophene-2-sulfonic acid (4-methyl-piperazinyl)-amide (0.14 g, 23%) as a yellow solid. MS (ISP) 326.3 [(M+H)+], mp 180° C.

b) Hydrogenation of a stirred solution of 5-chloro-4-nitro-thiophene-2-sulfonic acid (4-methyl-piperazinyl)-amide (0.39 g, 1.2 mmol) in methanol (40 ml) on Raney-Nickel (0.39 g) for 4 h at room temperature yielded after removal of the catalyst by filtration, evaporation and purification of the crude product by flash chromatography (dichloromethane/MeOH) the title compound (0.26 g, 73%) as a yellow solid. MS (ISP) 296.0 [(M+H)+], mp 91° C.

Example B.23

(RS)-1-(2-Amino-4-methyl-thiazole-5-sulfonyl)-pyrrolidin-3-ol a) To a stirred solution of (RS)-3-pyrrolidinol (0.51 g, 5.85 mmol) in THF (12 ml) was added at 0° C. (ice water bath) commercially available 2-acetamido-4-methylthiazole-5-sulfonyl chloride (1.0 g, 3.93 mmol) and triethylamine (0.6 ml, 4.32 mmol). The light yellow suspension was stirred at room temperature for 17 h, and evaporated. The crude product was further purified by flash chromatography on silica gel (dichloromethane/MeOH) and subsequent crystallization (dichloromethane/MeOH/hexane) to yield (RS)-1-(2-acetamido-4-methyl-thiazole-5-sulfonyl)-pyrrolidin-3-ol (0.82 g, 68%) as a white solid. MS (ISP) 306.3 [(M+H)+]; mp 241° C.

b) A stirred suspension of (RS)-1-(2-acetamido-4-methyl-thiazole-5-sulfonyl)-pyrrolidin-3-ol (0.82 g, 2.68 mmol) in 6N hydrochloric acid (13 ml) was heated for 2 h at 80° C. evaporated, and saturated NaHCO$_3$ solution (20 ml) was added. The mixture was extracted with ethyl acetate (3×50 ml), the combined organic layers washed with brine (50 ml), dried (MgSO$_4$) and evaporated. The crude product was further purified by crystallization (dichloromethane/MeOH/hexane) to yield the title compound (0.62 g, 88%) as a white solid. MS (ISP) 263.8 [(M+H)+]; mp 165° C.

Synthesis of Intermediates Compounds

Pyrazolo-pyrimidine Carboxylic Acids of Formula (VI) From Acetophenones

Some of the intermediates compounds, e.g. the pyrazolo-pyrimidine carboxylic acids derivatives which can be used according to the general procedures I and II are commercially available. However some of said intermediates have been prepared from acetophenones according to the procedures as outlined hereafter and unless otherwise specified, these compounds are novel. The person skilled in the art will be able to prepare other pyrazolo-pyrimidine carboxylic acids derivatives useful in the general procedures I and II taking into account the following examples of preparation:

Example C.1

7-Difluoromethyl-5-(4-trifluoromethyl-phenyl)-pyrazolo[1,5-a]pyrimidine-3-carboxylic acid a) To a stirred solution of ethyl difluoroacetate (5.0 ml, 21 mmol) in tert-butyl-methyl-ether (30 ml) was added at room temperature a 5.4M solution of sodium methanolate in methanol (4.65 ml, 25 mmol) followed by a solution of commercially available 4-trifluoromethyl-acetophenone (4.0 g, 21 mmol) in tert-butyl-methyl-ether (10 ml). The reaction mixture was stirred at room temperature for 19 h, poured into ice/water (50 ml), acidified with 2N HCl (40 ml) and extracted with diethyl ether (2×100 ml). The combined organic layers were washed with brine (2×50 ml), dried (MgSO$_4$) and evaporated to give crude 4,4-difluoro-1-(4-trifluoromethyl-phenyl)-butane-1,3-dione (5.87 g) as a yellow liquid, which was used without further purification.

b) A stirred mixture of commercially available 3-amino-4-ethoxycarbonyl-pyrazole (3.38 g, 22 mmol) and 4,4-difluoro-1-(4-trifluoromethyl-phenyl)-butane-1,3-dione (5.8 g, 22 mmol) in acetic acid (45 ml) was heated under reflux conditions for 1.5 h. The reaction mixture was evaporated and the crude product (yellow solid, 8.5 g, 22 mmol) was dissolved in a mixture of 2M KOH in methanol (176.5 ml, 0.35 mol) and water (85 ml). The reaction mixture was stirred at 60° C. for 1.5 h, poured into ice/water (200 ml), acidified with 3N sulfuric acid (pH=4) and stirred at room temperature for 30 min. The precipitate was collected by filtration and further purified by crystallization from diethylether/methanol to give the title compound (4.51 g, 57%) as an off-white solid. MS (ISP) 356.1 [(M−H)$^-$]; m.p. 261° C.

Example C.2

7-Trifluoromethyl-5-(4-trifluoromethyl-phenyl)-pyrazolo[1,5-a]pyrimidine-3-carboxylic acid The title compound was prepared from commercially available ethyl trifluoroacetate, commercially available 4-trifluoromethyl-acetophenone and commercially available 3-amino-4-ethoxycarbonyl-pyrazole according to the general procedure I.

Light yellow solid. MS (EI) 374.9 [M]; mp 248° C.

Example C.3

5-(4-Chloro-phenyl)-7-difluoromethyl-pyrazolo[1,5-a]pyrimidine-3-carboxylic acid The title compound was prepared from commercially available ethyl difluoroacetate, commercially available 4-chloro-acetophenone and commercially available 3-amino-4-ethoxycarbonyl-pyrazole according to the general procedure I. Off-white solid. MS (ISP) 322.2 [(M−H)$^-$]; mp 232° C.

Example C.4

5-(4-Chloro-phenyl)-7-trifluoromethyl-pyrazolo[1,5-a]pyrimidine-3-carboxylic acid The title compound was prepared from commercially available ethyl trifluoroacetate, commercially available 4-chloro-acetophenone and commercially available 3-amino-4-ethoxycarbonyl-pyrazole according to the general procedure I. Off-white solid. MS (ISP) 340.0 [(M−H)$^-$]; mp 238° C.

Example C.5

7-Difluoromethyl-5-(3-methyl-4-trifluoromethyl-phenyl)-pyrazolo[1,5-a]pyrimidine-3-carboxylic acid The title compound was prepared from commercially available ethyl difluoroacetate, 3-methyl-4-trifluoro-acetophenone (example A.4) and commercially available 3-amino-4-ethoxycarbonyl-pyrazole according to the general procedure I. Off-white solid. MS (ISP) 370.1 [(M−H)$^-$]; mp 217° C.

Example C.6

5-(4-Chloro-3-methyl-phenyl)-7-trifluoromethyl-pyrazolo[1,5-a]pyrimidine-3-carboxylic acid The title compound was prepared from commercially available ethyl trifluoroacetate, commercially available 4-chloro-3-methyl-acetophenone and commercially available 3-amino-4-ethoxycarbonyl-pyrazole according to the general procedure I. Off-white solid. MS (ISP) 354.0 [(M−H)$^-$]; mp 243° C.

Example C.7

5-(3,4-Dichloro-phenyl)-7-difluoromethyl-pyrazolo[1,5-a]pyrimidine-3-carboxylic acid The title compound was prepared from commercially available ethyl difluoroacetate, commercially available 3,4-dichloro-acetophenone and commercially available 3-amino-4-ethoxycarbonyl-pyrazole according to the general procedure I. Off-white solid. MS (ISP) 356.0 [(M−H)$^-$]; mp 263° C.

Example C.8

5-(3-Methyl-4-trifluoromethyl-phenyl)-7-trifluoromethyl-pyrazolo[1,5-a]pyrimidine-3-carboxylic acid The title compound was prepared from commercially available ethyl trifluoroacetate, 3-methyl-4-trifluoro-acetophenone (example A.4) and commercially available 3-amino-4-ethoxycarbonyl-pyrazole according to the general procedure I. Off-white solid. MS (ISP) 388.1 [(M−H)$^-$]; mp 250° C.

Example C.9

5-(3,4-Dichloro-phenyl)-7-trifluoromethyl-pyrazolo[1,5-a]pyrimidine-3-carboxylic acid The title compound was prepared from commercially available ethyl trifluoroacetate, commercially available 3,4-dichloro-acetophenone and commercially available 3-amino-4-ethoxycarbonyl-pyrazole according to the general procedure I. Light yellow solid. MS (ISP) 374.1 [(M−H)$^-$]; mp 264° C.

Example C.10

5-[3-(2,2,2-Trifluoro-ethoxy)-4-trifluoromethyl-phenyl]-7-trifluoromethyl-pyrazolo[1,5-a]pyrimidine-3-carboxylic acid The title compound was prepared from commercially available ethyl trifluoroacetate, 3-(2,2,2-trifluoroethoxy-4-trifluoro-acetophenone (Example A.6) and commercially available 3-amino-4-ethoxycarbonyl-pyrazole according to the general procedure I. Off-white solid. MS (ISP) 471.9 [(M−H)$^-$]; mp 264° C.

Example C.11

5-(3-Ethoxy-4-trifluoromethyl-phenyl)-7-trifluoromethyl-pyrazolo[1,5-a]pyrimidine-3-carboxylic acid The title compound was prepared from commercially available ethyl trifluoroacetate, 3-ethoxy-4-trifluoro-acetophenone (Example A.5) and commercially available 3-amino-4-ethoxycarbonyl-pyrazole according to the general procedure I. Off-white solid. MS (ISP) 418.0 [(M−H)⁻]; mp 264° C.

Example C.12

7-Difluoromethyl-5-(3-ethoxy-4-trifluoromethyl-phenyl)-pyrazolo[1,5-a]pyrimidine-3-carboxylic acid The title compound was prepared from commercially available ethyl difluoroacetate, 3-ethoxy-4-trifluoro-acetophenone (Example A.5) and commercially available 3-amino-4-ethoxycarbonyl-pyrazole according to the general procedure I. Yellow solid. MS (ISP) 400.2 [(M−H)⁻]; mp 247° C.

Example C.13

5-(4-Chloro-3-methyl-phenyl)-7-difluoromethyl-pyrazolo[1,5-a]pyrimidine-3-carboxylic acid The title compound was prepared from commercially available ethyl difluoroacetate, commercially available 4-chloro-3-methyl-acetophenone and commercially available 3-amino-4-ethoxycarbonyl-pyrazole according to the general procedure I. Light yellow solid. MS (ISP) 336.0 [(M−H)⁻]; mp 238° C.

Example C.14

7-Difluoromethyl-5-[3-(2,2,2-trifluoro-ethoxy)-4-trifluoromethyl-phenyl]-pyrazolo[1,5-a]pyrimidine-3-carboxylic acid The title compound was prepared from commercially available ethyl difluoroacetate, 3-(2,2,2-trifluoroethoxy)-4-trifluoro-acetophenone (Example A.6) and commercially available 3-amino-4-ethoxycarbonyl-pyrazole according to the general procedure I. Off-white solid. MS (ISP) 454.2 [(M−H)⁻]; mp 261° C.

Example C.15

5-(3-Chloro-4-trifluoromethyl-phenyl)-7-difluoromethyl-pyrazolo[1,5-a]pyrimidine-3-carboxylic acid The title compound was prepared from commercially available ethyl difluoroacetate, 3-chloro-4-trifluoromethyl-acetophenone [CAS-No. 129322-80-1] and commercially available 3-amino-4-ethoxycarbonyl-pyrazole according to the general procedure I.
Light red solid. MS (ISP) 390.2 [(M−H)⁻]; mp 216° C.

Example C.16

7-Difluoromethyl-5-(3-fluoro-4-trifluoromethyl-phenyl)-pyrazolo[1,5-a]pyrimidine-3-carboxylic acid The title compound was prepared from commercially available ethyl difluoroacetate, commercially available 3-fluoro-4-trifluoromethyl-acetophenone and commercially available 3-amino-4-ethoxycarbonyl-pyrazole according to the general procedure I.
Light brown solid. MS (ISP) 374.1 [(M−H)⁻]; mp 233° C.

Example C.17

5-(3-Chloro-4-trifluoromethyl-phenyl)-7-trifluoromethyl-pyrazolo[1,5-a]pyrimidine-3-carboxylic acid The title compound was prepared from commercially available ethyl trifluoroacetate, 3-chloro-4-trifluoromethyl-acetophenone [CAS-No. 129322-80-1] and commercially available 3-amino-4-ethoxycarbonyl-pyrazole according to the general procedure I.
Light yellow solid. MS (ISP) 408.0 [(M−H)⁻]; mp 244° C.

Example C.18

5-(3-Fluoro-4-trifluoromethyl-phenyl)-7-trifluoromethyl-pyrazolo[1,5-a]pyrimidine-3-carboxylic acid The title compound was prepared from commercially available ethyl trifluoroacetate, commercially available 3-fluoro-4-trifluoromethyl-acetophenone and commercially available 3-amino-4-ethoxycarbonyl-pyrazole according to the general procedure I.
Light yellow solid. MS (ISP) 392.0 [(M−H)⁻]; mp 212° C.

Example C.19

5-(4-Chloro-phenyl)-7-cyclopropyl-pyrazolo[1,5-a]pyrimidine-3-carboxylic acid a) A mixture of ethyl 3-(4-chloro-phenyl)-3-oxo-propionate (18.1 g, 0.080 mol) and ethyl 5-amino-1H-pyrazole-4-carboxylate (13.7 g, 0.088 mol) was stirred at 160° C. for 3 h. AcOEt (40 mL) and hexane (40 mL) were successively added to the cooled mixture and stirring was continued at 0° C. for 0.5 h. The crystals were isolated by filtration and the solid was triturated for 1.2 h with 0.2 N HCl (80 mL). The solid was filtered off, washed with water and dried to give ethyl 5-(4-chloro-phenyl)-7-hydroxy-pyrazolo[1,5-a]pyrimidine-3-carboxylate (13.3 g, 52%). White solid. MS (ISN) 316.3 [(M−H)⁻]; mp 190-192° C.

b) A mixture of 5-(4-chloro-phenyl)-7-hydroxy-pyrazolo[1,5-a]pyrimidine-3-carboxylate (9.53 g, 0.03 mol), phosphorous oxychloride (11.0 mL, 0.12 mol), and N,N-dimethylaniline (1.3 mL, 0.01 mol) was stirred for 2 h at 100° C. The mixture was evaporated in vacuo and the residue was partitioned between water and dichloromethane. The organic phase was washed with water, dried (Na₂SO₄) and evaporated in vacuo. The remaining solid was crystallized from AcOEt/hexane to give 7-chloro-5-(4-chloro-phenyl)-pyrazolo[1,5-a]pyrimidine (6.80 g, 67%). Pale-yellow solid. MS (ISP) 336.0 [(M+H)⁺]; mp 133-135° C.

c) To a solution of 7-chloro-5-(4-chloro-phenyl)-pyrazolo[1,5-a]pyrimidine (4.0 g, 12.0 mmol), tetrakis(triphenylphosphin)palladium (1.15 g, 1.0 mmol) in THF (20 mL)

was added at 20° C. 0.25 M cyclopropylzinc chloride/THF suspension (ca.192 mL, 48 mmol; freshly prepared by stirring a mixture of 96 mL of 0.5 M cyclopropylmagnesium bromide/THF and 96 mL of 0.5 M zinc chloride/THF (96 mL) for 1 h at 0° C. followed by 1 h at 20° C.) and the mixture was refluxed in an atmosphere of argon for 2.5 h. After the slow addition at 0° C. of sat. aqueous NH$_4$Cl solution (30 mL), the mixture was partitioned between AcOEt and 10% sodium chloride solution. The organic layer was evaporated in vacuo and the residue was chromatographed on silica gel using AcOEt/cyclohexane (1:4 v/v) as eluent to give after crystallization from AcOEt the title compound (2.54 g, 62%). Off-white solid. MS (ISP) 342.1 [(M+H)$^+$]; mp 141-143° C.

d) A mixture of ethyl 5-(4-chloro-phenyl)-7-cyclopropyl-pyrazolo[1,5-a]pyrimidine-3-carboxylic acid (0.95 g, 2.8 mmol) and 2 N NaOH solution (5.6 mL) in MeOH (35 mL) was heated to 80° C. for 0.5 h. The mixture was cooled, diluted with water (150 mL) and washed with diethyl ether. The aqueous layer was acidified by the addition of 3N HCl to pH 2. The precipitate formed was isolated by filtration, washed with water, and dried to give the title compound (0.75 g, 86%). Off-white solid. MS (ISN) 312.3 [(M−H)$^−$]; mp 256° C.

Synthesis of the Compounds of the Invention

Example 1

7-Difluoromethyl-5-(4-trifluoromethyl-phenyl)-pyrazolo[1,5-a]pyrimidine-3-carboxylic-acid (2-chloro-5-sulfamoyl-thiophen-3-yl)-amide The title compound was prepared from 7-difluoromethyl-5-(4-trifluoromethyl-phenyl)-pyrazolo[1,5-a]pyrimidine-3-carboxylic acid (example C.1) and 4-amino-5-chloro-thiophene-2-sulfonic acid amide (example B.1) according to general procedure II. Light brown solid. MS (ISP) 549.9 [(M−H)$^−$]; mp 298° C.

Example 2

7-Trifluoromethyl-5-(4-trifluoromethyl-phenyl)-pyrazolo[1,5-a]pyrimidine-3-carboxylic acid (2-chloro-5-sulfamoyl-thiophen-3-yl)-amide The title compound was prepared from 7-trifluoromethyl-5-(4-trifluoromethyl-phenyl)-pyrazolo[1,5-a]pyrimidine-3-carboxylic acid (example C. 1) and 4-amino-5-chloro-thipohene-2-sulfonic acid amide (example B.1) according to general procedure II. Light brown solid. MS (ISP) 567.9 [(M+H)$^+$]; mp 275° C.

Example 3

7-Difluoromethyl-5-(4-trifluoromethyl-phenyl)-pyrazolo[1,5-a]pyrimidine-3-carboxylic acid (5-sulfamoyl-[1,3,4]thiadiazol-2-yl)-amide The title compound was prepared from 7-difluoromethyl-5-(4-trifluoromethyl-phenyl)-pyrazolo[1,5-a]pyrimidine-3-carboxylic acid (example C. 1) and 5-amino-[1,3,4]thiadiazole-2-sulfonic acid amide [commercially available, CAS 14949-00-9] according to general procedure II.
Light yellow solid. MS (ISP) 518.0 [(M−H)$^−$]; mp 284° C.

Example 4

7-Trifluoromethyl-5-(4-trifluoromethyl-phenyl)-pyrazolo[1,5-a]pyrimidine-3-carboxylic acid (5-sulfamoyl-[1,3,4]thiadiazol-2-yl)-amide The title compound was prepared from 7-trifluoromethyl-5-(4-trifluoromethyl-phenyl)-pyrazolo[1,5-a]pyrimidine-3-carboxylic acid (example C.1) and 5-amino-[1,3,4]thiadiazole-2-sulfonic acid amide [commercially available, CAS 14949-00-9] according to general procedure II.
Light yellow solid. MS (ISP) 536.1 [(M−H)$^−$]; mp 280° C.

Example 5

7-Difluoromethyl-5-(4-trifluoromethyl-phenyl)-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 7-difluoromethyl-5-(4-trifluoromethyl-phenyl)-pyrazolo[1,5-a]pyrimidine-3-carboxylic acid (example C.1) and 4-amino-5-chloro-thiophene-2-sulfonic acid (2-hydroxy-1,1-dimethyl-ethyl)-amide (example B.2) according to general procedure II.
Light yellow solid. MS (ISP) 622.2 [(M−H)$^−$]; mp 233° C.

Example 6

7-Trifluoromethyl-5-(4-trifluoromethyl-phenyl)-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 7-trifluoromethyl-5-(4-trifluoromethyl-phenyl)-pyrazolo[1,5-a]pyrimidine-3-carboxylic acid (example C. 1) and 4-amino-5-chloro-thiophene-2-sulfonic acid (2-hydroxy-1,1-dimethyl-ethyl)-amide (example B.2) according to general procedure II.
Light yellow solid. MS (ISP) 640.1 [ (M+H)$^+$]; mp 223° C.

Example 7

7-Difluoromethyl-5-(4-trifluoromethyl-phenyl)-pyrazolo[1,5-a]pyrimidine-3-carboxylic acid (4-methyl-5-sulfamoyl-thiazol-2-yl)-amide The title compound was prepared from 7-difluoromethyl-5-(4-trifluoromethyl-phenyl)-pyrazolo[1,5-a]pyrimidine-3-carboxylic acid (example C.1) and 2-amino-4-methyl-thiazole-2-sulfonic acid amide [CAS-No. 187230-38-2] according to general procedure II. Light yellow solid. MS (ISP) 531.0 [(M−H)$^−$]; mp 284° C.

Example 8

7-Trifluoromethyl-5-(4-trifluoromethyl-phenyl)-pyrazolo[1,5-a]pyrimidine-3-carboxylic acid (4-methyl-5-sulfamoyl-thiazol-2-yl)-amide The title compound was prepared from 7-trifluoromethyl-5-(4-trifluoromethyl-phenyl)-pyrazolo[1,5-a]pyrimidine-3-carboxylic acid (example C. 1) and 2-amino-4-methyl-thiazole-2-sulfonic acid amide [CAS-No. 187230-38-2] according to general procedure II. Yellow solid. MS (ISP) 549.0 [(M−H)⁻]; mp 303° C.

Example 9

5-(4-Chloro-phenyl)-7-trifluoromethyl-pyrazolo[1,5-a]pyrimidine-3-carboxylic acid (2-chloro-5-sulfamoyl-thiophen-3-yl)-amide The title compound was prepared from 5-(4-chloro-phenyl)-7-trifluoromethyl-pyrazolo[1,5-a]pyrimidine-3-carboxylic acid (example C.4) and 4-amino-5-chloro-thipohene-2-sulfonic acid amide (example B.1) according to general procedure II. Yellow solid. MS (ISP) 534.0 [(M−H)⁻]; mp 329° C.

Example 10

5-(3-Ethoxy-4-trifluoromethyl-phenyl)-7-trifluoromethyl-pyrazolo[1,5-a]pyrimidine-3-carboxylic acid (2-chloro-5-sulfamoyl-thiophen-3-yl)-amide The title compound was prepared from 5-(3-ethoxy-4-trifluoromethyl-phenyl)-7-trifluoromethyl-pyrazolo[1,5-a]pyrimidine-3-carboxylic acid (example C.10) 4-amino-5-chloro-thipohene-2-sulfonic acid amide (example B.1) according to general procedure II. Yellow solid. MS (ISP) 612.2 [(M−H)⁻]; mp 281° C.

Example 11

5-(3-Methyl-4-trifluoromethyl-phenyl)-7-trifluoromethyl-pyrazolo[1,5-a]pyrimidine-3-carboxylic acid (2-chloro-5-sulfamoyl-thiophen-3-yl)-amide The title compound was prepared from 5-(3-methyl-4-trifluoromethyl-phenyl)-7-trifluoromethyl-pyrazolo[1,5-a]pyrimidine-3-carboxylic acid (example C.8) and 4-amino-5-chloro-thipohene-2-sulfonic acid amide (example B.1) according to general procedure II. Yellow solid. MS (ISP) 581.8 [(M−H)⁻]; mp 283° C.

Example 12

5-(4-Chloro-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 5-(4-chloro-phenyl)-7-trifluoromethyl-pyrazolo[1,5-a]pyrimidine-3-carboxylic acid (example C.4) and 4-amino-5-chloro-thiophene-2-sulfonic acid (2-hydroxy-1,1-dimethyl-ethyl)-amide (example B.2) according to general procedure II. Yellow solid. MS (ISP) 605.8 [(M−H)⁻]; mp 272° C.

Example 13

7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 7-trifluoromethyl-5-(4-trifluoromethyl-phenyl)-pyrazolo[1,5-a]pyrimidine-3-carboxylic acid (example C. 1) and 2-amino-4-methyl-thiazole-5-sulfonic acid (2-hydroxy-1,1-dimethyl-ethyl)-amide (example B.3) according to general procedure II. Yellow solid. MS (ISP) 621.0 [(M−H)⁻]; mp 257° C.

Example 14

7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-hydroxy-1,1-dimethyl-ethyl)-amide (example B.3) according to general procedure II. Yellow solid. MS (ISP) 603.0 [(M−H)⁻]; mp 268° C.

Example 15

5-(3-Ethoxy-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 5-(3-ethoxy-4-trifluoromethyl-phenyl)-7-trifluoromethyl-pyrazolo[1,5-a]pyrimidine-3-carboxylic acid (example C.10) and 4-amino-5-chloro-thiophene-2-sulfonic acid (2-hydroxy-1,1-dimethyl-ethyl)-amide (example B.2) according to general procedure II. Yellow solid. MS (ISP) 684.3 [(M−H)⁻]; mp 234° C.

Example 16

5-(3-Methyl-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 5-(3-methyl-4-trifluoromethyl-phenyl)-7-trifluoromethyl-pyrazolo[1,5-a]pyrimidine-3-carboxylic acid (example C.8) and 4-amino-5-chloro-thiophene-2-sulfonic acid (2-hydroxy-1,1-dimethyl-ethyl)-amide (example B.2) according to general procedure II. Yellow solid. MS (ISP) 654.2 [(M−H)⁻]; mp 207° C.

Example 17

5-[3-(2,2,2-Trifluoro-ethoxy)-4-trifluoromethyl-phenyl]-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) and 4-amino-5-chloro-thiophene-2-sulfonic acid (2-hydroxy-1,1-dimethyl-ethyl)-amide (example B.2) according to general procedure II.

Yellow solid. MS (ISP) 738.3 [(M−H⁻]; mp 264° C.

Example 18

5-(3-Chloro-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 5-(3-chloro-4-trifluoromethyl-phenyl)-7-trifluoromethyl-pyrazolo[1,5-a]pyrimidine-3-carboxylic acid (example C.17) and 4-amino-5-chloro-thiophene-2-sulfonic acid (2-hydroxy-1,1-dimethyl-ethyl)-amide (example B.2) according to general procedure II.
Yellow solid. MS (ISP) 674.3 [(M+H)$^+$]; mp 254° C.

Example 19

5-(4-Chloro-phenyl)-7-trifluoromethyl-pyrazolo[1,5-a]pyrimidine-3-carboxylic acid (4-methyl-5-sulfamoyl-thiazol-2-yl)-amide The title compound was prepared from 5-(4-chloro-phenyl)-7-trifluoromethyl-pyrazolo[1,5-a]pyrimidine-3-carboxylic acid (example C.4) and 2-amino-4-methyl-thiazole-2-sulfonic acid amide [CAS-No. 187230-38-2] according to general procedure II. Yellow solid. MS (ISP) 515.0 [(M–H)$^-$]; mp 305° C.

Example 20

5-(3-Ethoxy-4-trifluoromethyl-phenyl)-7-trifluoromethyl-pyrazolo[1,5-a]pyrimidine-3-carboxylic acid (4-methyl-5-sulfamoyl-thiazol-2-yl)-amide The title compound was prepared from 5-(3-ethoxy-4-trifluoromethyl-phenyl)-7-trifluoromethyl-pyrazolo[1,5-a]pyrimidine-3-carboxylic acid (example C.10) and 2-amino-4-methyl-thiazole-2-sulfonic acid amide [CAS-No. 187230-38-2] according to general procedure II. Yellow solid. MS (ISP) 595.4 [(M+H)$^+$]; mp 300° C.

Example 21

5-(3-Methyl-4-trifluoromethyl-phenyl)-7-trifluoromethyl-pyrazolo[1,5-a]pyrimidine-3-carboxylic acid (4-methyl-5-sulfamoyl-thiazol-2-yl)-amide The title compound was prepared from 5-(3-methyl-4-trifluoromethyl-phenyl)-7-trifluoromethyl-pyrazolo[1,5-a]pyrimidine-3-carboxylic acid (example C.8) and 2-amino-4-methyl-thiazole-2-sulfonic acid amide [CAS-No. 187230-38-2] according to general procedure II. Yellow solid. MS (ISP) 563.3 [(M–H)$^-$]; mp 309° C.

Example 22

5-(4-Chloro-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 5-(4-chloro-phenyl)-7-trifluoromethyl-pyrazolo[1,5-a]pyrimidine-3-carboxylic acid (example C.4) and 2-amino-4-methyl-thiazole-5-sulfonic acid (2-hydroxy-1,1-dimethyl-ethyl)-amide (example B.3) according to general procedure II. Yellow solid. MS (ISP) 587.1 [(M+H)$^+$]; mp 274° C.

Example 23

5-(3-Ethoxy-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 5-(3-ethoxy-4-trifluoromethyl-phenyl)-7-trifluoromethyl-pyrazolo[1,5-a]pyrimidine-3-carboxylic acid (example C.10) and 2-amino-4-methyl-thiazole-5-sulfonic acid (2-hydroxy-1,1-dimethyl-ethyl)-amide (example B.3) according to general procedure II. Light yellow solid. MS (ISP) 665.2 [(M–H)$^-$]; mp 276° C.

Example 24

5-(3-Methyl-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 5-(3-methyl-4-trifluoromethyl-phenyl)-7-trifluoromethyl-pyrazolo[1,5-a]pyrimidine-3-carboxylic acid (example C.8) and 2-amino-4-methyl-thiazole-5-sulfonic acid (2-hydroxy-1,1-dimethyl-ethyl)-amide (example B.3) according to general procedure II. Yellow solid. MS (ISP) 635.0 [(M+H)$^+$]; mp 272° C.

Example 25

5-(3-Chloro-4-trifluoromethyl-phenyl)-7-trifluoromethyl-pyrazolo[1,5-a]pyrimidine-3-carboxylic acid (4-methyl-5-sulfamoyl-thiazol-2-yl)-amide The title compound was prepared from 5-(3-chloro-4-trifluoromethyl-phenyl)-7-trifluoromethyl-pyrazolo[1,5-a]pyrimidine-3-carboxylic acid (example C.17) and 2-amino-4-methyl-thiazole-2-sulfonic acid amide [CAS-No. 187230-38-2] according to general procedure II.
Light brown solid. MS (ISP) 585.1 [(M+H)$^+$]; mp 299° C.

Example 26

5-(3,4-Dichloro-phenyl)-7-trifluoromethyl-pyrazolo[1,5-a]pyrimidine-3-carboxylic acid (4-methyl-5-sulfamoyl-thiazol-2-yl)-amide The title compound was prepared from 5-(3,4-dichloro-phenyl)-7-trifluoromethyl-pyrazolo[1,5-a]pyrimidine-3-carboxylic acid (example C.9) and 2-amino-4-methyl-thiazole-2-sulfonic acid amide [CAS-No. 187230-38-2] according to general procedure II. Yellow solid. MS (ISP) 549.2 [(M–H)$^-$]; mp 307° C.

Example 27

5-[3-(2,2,2-Trifluoro-ethoxy)-4-trifluoromethyl-phenyl]-7-trifluoromethyl-pyrazolo[1,5-a]pyrimidine-3-carboxylic acid (4-methyl-5-sulfamoyl-thiazol-2-yl)-amide The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) and 4-amino-5-chloro-thiophene-2-sulfonic acid (2-hydroxy-1-hydroxymethyl-ethyl)-amide (example B.4) according to general procedure II. Yellow solid. MS (ISP) 649.1 [(M+H)⁺]; mp 264° C.

Example 28

7-Difluoromethyl-5-(4-trifluoromethyl-phenyl)-pyrazolo[1,5-a]pyrimidine-3-carboxylic acid [2-chloro-5-(2-hydroxy-1-hydroxymethyl-ethylsulfamoyl)-thiophen-3-yl]-amide The title compound was prepared from 7-difluoromethyl-5-(4-trifluoromethyl-phenyl)-pyrazolo[1,5-a]pyrimidine-3-carboxylic acid (example C.1) and 4-amino-5-chloro-thiophene-2-sulfonic acid (2-hydroxy-1-hydroxymethyl-ethyl)-amide (example B.4) according to general procedure II. Light yellow solid. MS (ISP) 624.2 [(M−H)⁻]; mp 241° C.

Example 29

7-Trifluoromethyl-5-(4-trifluoromethyl-phenyl)-pyrazolo[1,5-a]pyrimidine-3-carboxylic acid [2-chloro-5-(2-hydroxy-1-hydroxymethyl-ethylsulfamoyl)-thiophen-3-yl]-amide The title compound was prepared from 7-trifluoromethyl-5-(4-trifluoromethyl-phenyl)-pyrazolo[1,5-a]pyrimidine-3-carboxylic acid (example C.1) and 4-amino-5-chloro-thiophene-2-sulfonic acid (2-hydroxy-1-hydroxymethyl-ethyl)-amide (example B.4) according to general procedure II. Yellow solid. MS (ISP) 642.2 [(M−H)⁻]; mp 225° C.

Example 30

5-(3-Chloro-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 5-(3-chloro-4-trifluoromethyl-phenyl)-7-trifluoromethyl-pyrazolo[1,5-a]pyrimidine-3-carboxylic acid (example C.17) and 2-amino-4-methyl-thiazole-5-sulfonic acid (2-hydroxy-1,1-dimethyl-ethyl)-amide (example B.3) according to general procedure II. Yellow solid. MS (ISP) 655.1 [(M−H)⁻]; mp 274° C.

Example 31

5-(3,4-Dichloro-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 5-(3,4-dichloro-phenyl)-7-trifluoromethyl-pyrazolo[1,5-a]pyrimidine-3-carboxylic acid (example C.9) and 2-amino-4-methyl-thiazole-5-sulfonic acid (2-hydroxy-1,1-dimethyl-ethyl)-amide (example B.3) according to general procedure II. Yellow solid. MS (ISP) 621.0 [(M−H)⁻]; mp 265° C.

Example 32

5-[3-(2,2,2-Trifluoro-ethoxy)-4-trifluoromethyl-phenyl]-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) and 2-amino-4-methyl-thiazole-5-sulfonic acid (2-hydroxy-1,1-dimethyl-ethyl)-amide (example B.3) according to general procedure II.
Yellow solid. MS (ISP) 719.3 [(M−H)⁻]; mp 275° C.

Example 33

7-Difluoromethyl-5-(3-methyl-4-trifluoromethyl-phenyl)-pyrazolo[1,5-a]pyrimidine-3-carboxylic acid (4-methyl-5-sulfamoyl-thiazol-2-yl)-amide The title compound was prepared from 7-difluoromethyl-5-(3-methyl-4-trifluoromethyl-phenyl)-pyrazolo[1,5-a]pyrimidine-3-carboxylic acid (example C.5) and 2-amino-4-methyl-thiazole-2-sulfonic acid amide [CAS-No. 187230-38-2] according to general procedure II. Yellow solid. MS (ISP) 545.1 [(M−H)⁻]; mp 307° C.

Example 34

7-Difluoromethyl-5-(4-trifluoromethyl-phenyl)-pyrazolo[1,5-a]pyrimidine-3-carboxylic acid {5-[bis-(2-hydroxy-ethyl)-sulfamoyl]-2-chloro-thiophen-3-yl}-amide The title compound was prepared from 7-difluoromethyl-5-(4-trifluoromethyl-phenyl)-pyrazolo[1,5-a]pyrimidine-3-carboxylic acid (example C.1) and 4-amino-5-chloro-thiophene-2-sulfonic acid bis-(2-hydroxy-ethyl)-amide (example B.5) according to general procedure II. Light yellow solid. MS (ISP) 640.3 [(M+H)⁺]; mp 216° C.

Example 35

7-Trifluoromethyl-5-(4-trifluoromethyl-phenyl)-pyrazolo[1,5-a]pyrimidine-3-carboxylic acid {5-[bis-(2-hydroxy-ethyl)-sulfamoyl]-2-chloro-thiophen-3-yl}-amide The title compound was prepared from 7-trifluoromethyl-5-(4-trifluoromethyl-phenyl)-pyrazolo[1,5-a]pyrimidine-3-carboxylic acid (example C. 1) and 4-amino-5-chloro-thiophene-2-sulfonic acid bis-(2-hydroxy-ethyl)-amide (example B.5) according to general procedure II.
Yellow solid. MS (ISP) 658.4 [(M+H)⁺]; mp 217° C.

Example 36

7-Trifluoromethyl-5-(4-trifluoromethyl-phenyl)-pyrazolo[1,5-a]pyrimidine-3-carboxylic acid [2-chloro-5-(2-hydroxy-ethylsulfamoyl)-thiophen-3-yl]-amide The title compound was prepared from 7-trifluoromethyl-5-(4-trifluoromethyl-phenyl)-pyrazolo[1,5-a]pyrimidine-3-carboxylic acid (example C. 1) and 4-amino-5-chloro-thiophene-2-sulfonic acid (2-hydroxy-ethyl)-amide (example B.6) according to general procedure II. Yellow solid. MS (ISP) 612.0 [(M−H)⁻]; mp 191° C.

Example 37

7-Difluoromethyl-5-(4-trifluoromethyl-phenyl)-pyrazolo[1,5-a]pyrimidine-3-carboxylic acid [2-chloro-5-(2-hydroxy-1-hydroxymethyl-1-methyl-ethylsulfamoyl)-thiophen-3-yl]-amide The title compound was prepared from 7-difluoromethyl-5-(4-trifluoromethyl-phenyl)-pyrazolo[1,5-a]pyrimidine-3-carboxylic acid (example C.1) and 4-amino-5-chlorothiophene-2-sulfonic acid (2-hydroxy-1-hydroxymethyl-1-methyl-ethyl)-amide (example B.7) according to general procedure II. Light yellow solid. MS (ISP) 638.0 [(M−H)⁻]; mp 237° C.

Example 38

7-Trifluoromethyl-5-(4-trifluoromethyl-phenyl)-pyrazolo[1,5-a]pyrimidine-3-carboxylic acid [2-chloro-5-(2-hydroxy-1-hydroxymethyl-1-methyl-ethylsulfamoyl)-thiophen-3-yl]-amide The title compound was prepared from 7-trifluoromethyl-5-(4-trifluoromethyl-phenyl)-pyrazolo[1,5-a]pyrimidine-3-carboxylic acid (example C.1) and 4-amino-5-chlorothiophene-2-sulfonic acid (2-hydroxy-1-hydroxymethyl-1-methyl-ethyl)-amide (example B.7) according to general procedure II. Yellow solid. MS (ISP) 656.0 [(M−H)⁻]; mp 201° C.

Example 39

7-Difluoromethyl-5-(3-methyl-4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 7-difluoromethyl-5-(3-methyl-4-trifluoromethyl-phenyl)-pyrazolo[1,5-a]pyrimidine-3-carboxylic acid (example C.8) and 2-amino-4-methyl-thiazole-5-sulfonic acid (2-hydroxy-1,1-dimethyl-ethyl)-amide (example B.3) according to general procedure II. Yellow solid. MS (ISP) 617.2 [(M−H)⁻]; mp 271° C.

Example 40

7-Difluoromethyl-5-(4-trifluoromethyl-phenyl)-pyrazolo[1,5-a]pyrimidine-3-carboxylic acid {5-[bis-(2-hydroxy-ethyl)-sulfamoyl]-4-methyl-thiazol-2-yl}-amide The title compound was prepared from 7-difluoromethyl-5-(4-trifluoromethyl-phenyl)-pyrazolo[1,5-a]pyrimidine-3-carboxylic acid (example C. 1) and 2-amino-4-methyl-thiazole-5-sulfonic acid bis-(2-hydroxy-ethyl)-amide (example B.8) according to general procedure II. Light yellow solid. MS (ISP) 621.1 [(M+H)⁺]; mp 191° C.

Example 41

7-Trifluoromethyl-5-(4-trifluoromethyl-phenyl)-pyrazolo[1,5-a]pyrimidine-3-carboxylic acid {5-[bis-(2-hydroxy-ethyl)-sulfamoyl]-4-methyl-thiazol-2-yl}-amide The title compound was prepared from 7-trifluoromethyl-5-(4-trifluoromethyl-phenyl)-pyrazolo[1,5-a]pyrimidine-3-carboxylic acid (example C. 1) and 2-amino-4-methyl-thiazole-5-sulfonic acid bis-(2-hydroxy-ethyl)-amide (example B.8) according to general procedure II.
Yellow solid. MS (ISP) 639.1 [(M+H)⁺]; mp 214° C.

Example 42

7-Trifluoromethyl-5-(4-trifluoromethyl-phenyl)-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide The title compound was prepared from 7-trifluoromethyl-5-(4-trifluoromethyl-phenyl)-pyrazolo[1,5-a]pyrimidine-3-carboxylic acid (example C. 1) and 2-amino-4-methyl-thiazole-5-sulfonic acid (2-hydroxy-1-hydroxymethyl-1-methyl-ethyl)-amide (example B.9) according to general procedure II. Yellow solid. MS (ISP) 637.0 [(M−H)⁻]; mp 250° C.

Example 43

7-Difluoromethyl-5-(4-trifluoromethyl-phenyl)-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-hydroxy-1-hydroxymethyl-1-methyl-ethyl)-amide (example B.9) according to general procedure II. Yellow solid. MS (ISP) 619.2 [(M−H)⁻]; mp 248° C.

Example 44

7-Difluoromethyl-5-(4-trifluoromethyl-phenyl)-pyrazolo[1,5-a]pyrimidine-3-carboxylic acid [2-chloro-5-(2-hydroxy-ethylsulfamoyl)-thiophen-3-yl]-amide The title compound was prepared from 7-difluoromethyl-5-(4-trifluoromethyl-phenyl)-pyrazolo[1,5-a]pyrimidine-3-carboxylic acid (example C. 1) and 4-amino-5-chlorothiophene-2-sulfonic acid (2-hydroxy-ethyl)-amide (example B.6) according to general procedure II. Yellow solid. MS (ISP) 594.1.2 [(M−H)⁻]; mp 209° C.

Example 45

7-Difluoromethyl-5-(4-trifluoromethyl-phenyl)-pyrazolo[1,5-a]pyrimidine-3-carboxylic acid [5-(2-hydroxy-ethylsulfamoyl)-4-methyl-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-hydroxy-ethyl)-amide (example B.10) according to general procedure II. Yellow solid. MS (ISP) 575.1 [(M–H)⁻]; mp 134° C.

Example 46

7-Trifluoromethyl-5-(4-trifluoromethyl-phenyl)-pyrazolo[1,5-a]pyrimidine-3-carboxylic acid [5-(2-hydroxy-ethylsulfamoyl)-4-methyl-thiazol-2-yl]-amide The title compound was prepared from 7-trifluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-hydroxy-ethyl)-amide (example B.10) according to general procedure II. Yellow solid, MS (ISP) 593.1 [(M–H)⁻]; mp 166° C.

Example 47

7-Trifluoromethyl-5-(4-trifluoromethyl-phenyl)-pyrazolo[1,5-a]pyrimidine-3-carboxylic acid (2-methyl-5-sulfamoyl-thiophen-3-yl)-amide The title compound was prepared from 7-trifluoromethyl-5-(4-trifluoromethyl-phenyl)-pyrazolo[1,5-a]pyrimidine-3-carboxylic acid (example C.1) and 4-amino-5-methyl-thiophene-2-sulfonic acid amide (example B.11) according to general procedure II. Yellow solid. MS (ISP) 548.1 [(M–H)⁻]; mp 297° C.

Example 48

7-Difluoromethyl-5-(4-trifluoromethyl-phenyl)-pyrazolo[1,5-a]pyrimidine-3-carboxylic acid (2-methyl-5-sulfamoyl-thiophen-3-yl)-amide The title compound was prepared from 7-difluoromethyl-5-(4-trifluoromethyl-phenyl)-pyrazolo[1,5-a]pyrimidine-3-carboxylic acid (example C.1) and 4-amino-5-methyl-thiophene-2-sulfonic acid amide (example B.11) according to general procedure II. Yellow solid. MS (ISP) 530.0 [(M–H)⁻]; mp 313° C.

Example 49

7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-2-methyl-thiophen-3-yl]-amide The title compound was prepared from 7-trifluoromethyl-5-(4-trifluoromethyl-phenyl)-pyrazolo[1,5-a]pyrimidine-3-carboxylic acid (example C. 1) and 4-amino-5-methyl-thiophene-2-sulfonic acid (2-hydroxy-1,1-dimethyl-ethyl)-amide (example B.12) according to general procedure II. Yellow solid. MS (ISP) 620.3 [(M–H)⁻]; mp 225° C.

Example 50

7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-2-methyl-thiophen-3-yl]-amide The title compound was prepared from 7-difluoromethyl-5-(4-trifluoromethyl-phenyl)-pyrazolo[1,5-a]pyrimidine-3-carboxylic acid (example C.1) and 4-amino-5-methyl-thiophene-2-sulfonic acid (2-hydroxy-1,1-dimethyl-ethyl)-amide (example B.12) according to general procedure II. Yellow solid. MS (ISP) 602.2 [(M–H)⁻]; mp 180° C.

Example 51

7-Trifluoromethyl-5-(4-trifluoromethyl-phenyl)-pyrazolo[1,5-a]pyrimidine-3-carboxylic acid (5-sulfamoyl-thiazol-2-yl)-amide The title compound was prepared from 7-trifluoromethyl-5-(4-trifluoromethyl-phenyl)-pyrazolo[1,5-a]pyrimidine-3-carboxylic acid (example C.1) and 2-amino-thiazole-5-sulfonic acid amide [CAS-No. 63735-95-5] according to general procedure II. Yellow solid. MS (ISP) 535.2 [(M–H)⁻]; mp 309° C.

Example 52

7-Difluoromethyl-5-(4-trifluoromethyl-phenyl)-pyrazolo[1,5-a]pyrimidine-3-carboxylic acid (5-sulfamoyl-thiazol-2-yl)-amide The title compound was prepared from 7-difluoromethyl-5-(4-trifluoromethyl-phenyl)-pyrazolo[1,5-a]pyrimidine-3-carboxylic acid (example C. 1) and 2-amino-thiazole-5-sulfonic acid amide [CAS-No. 63735-95-5] according to general procedure II. Light yellow solid. MS (ISP) 517.2 [(M–H)⁻]; mp 311° C.

Example 53

5-(3-Ethoxy-4-trifluoromethyl-phenyl)-7-trifluoromethyl-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide The title compound was prepared from 5-(3-ethoxy-4-trifluoromethyl-phenyl)-7-trifluoromethyl-pyrazolo[1,5-a]pyrimidine-3-carboxylic acid (example C.10) and 2-amino-4-methyl-thiazole-5-sulfonic acid (2-hydroxy-1-hydroxymethyl-1-methyl-ethyl)-amide (example B.9) according to general procedure II. Light yellow solid. MS (ISP) 681.2 [(M–H)⁻]; mp 220° C.

Example 54

7-Difluoromethyl-5-(4-trifluoromethyl-phenyl)-pyrazolo[1,5-a]pyrimidine-3-carboxylic acid [2-chloro-5-(2-dimethylamino-ethylsulfamoyl)-thiophen-3-yl]-amide The title compound was prepared from 7-difluoromethyl-5-(4-trifluoromethyl-phenyl)-pyrazolo[1,5-a]pyrimidine-3-carboxylic acid (example C. 1) and 4-amino-5-chloro-thiophene-2-sulfonic acid (2-dimethylamino-ethyl)-amide (example B.14) according to general procedure II.

Yellow solid. MS (ISP) 623.1 [(M–H)⁻]; mp 162° C.

Example 55

7-Trifluoromethyl-5-(4-trifluoromethyl-phenyl)-pyrazolo[1,5-a]pyrimidine-3-carboxylic acid [2-chloro-5-(2-dimethylamino-ethylsulfamoyl)-thiophen-3-yl]-amide The title compound was prepared from 7-trifluoromethyl-5-(4-trifluoromethyl-phenyl)-pyrazolo[1,5-a]pyrimidine-3-carboxylic acid (example C.1) and 4-amino-5-chloro-thiophene-2-sulfonic acid (2-dimethylamino-ethyl)-amide (example B.14) according to general procedure II.
Yellow solid. MS (ISP) 639.1 [(M−H)⁻]; mp 198° C.

Example 56

5-(3-Ethoxy-4-trifluoromethyl-phenyl)-7-trifluoromethyl-pyrazolo[1,5-a]pyrimidine-3-carboxylic acid [2-chloro-5-(2-hydroxy-ethylsulfamoyl)-thiophen-3-yl]-amide The title compound was prepared from 5-(3-ethoxy-4-trifluoromethyl-phenyl)-7-trifluoromethyl-pyrazolo[1,5-a]pyrimidine-3-carboxylic acid (example C.10) and 4-amino-5-chloro-thiophene-2-sulfonic acid (2-hydroxy-ethyl)-amide (example B.6) according to general procedure II. Light yellow solid. MS (ISP) 656.0 [(M−H)⁻]; mp 250° C.

Example 57

7-Difluoromethyl-5-(4-trifluoromethyl-phenyl)-pyrazolo[1,5-a]pyrimidine-3-carboxylic acid [5-(2-dimethylamino-ethylsulfamoyl)-4-methyl-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-dimethylamino-ethyl)-amide (example B.15) according to general procedure II.
Yellow solid. MS (ISP) 602.1 [(M−H)⁻]; mp 217° C.

Example 58

7-Trifluoromethyl-5-(4-trifluoromethyl-phenyl)-pyrazolo[1,5-a]pyrimidine-3-carboxylic acid [5-(2-dimethylamino-ethylsulfamoyl)-4-methyl-thiazol-2-yl]-amide The title compound was prepared from 7-trifluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-dimethylamino-ethyl)-amide (example B.15) according to general procedure II.
Yellow solid. MS (ISP) 620.2 [(M−H)⁻]; mp 235° C.

Example 59

7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-thiazol-2-yl]-amide The title compound was prepared from 7-trifluoromethyl-5-(4-trifluoromethyl-phenyl)-pyrazolo[1,5-a]pyrimidine-3-carboxylic acid (example C. 1) and 2-amino-thiazole-5-sulfonic acid (2-hydroxy-1,1-dimethyl-ethyl)-amide (example B.13) according to general procedure II. Yellow solid. MS (ISP) 607.0 [(M−H)⁻]; mp 292° C.

Example 60

7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and 2-amino-thiazole-5-sulfonic acid (2-hydroxy-1,1-dimethyl-ethyl)-amide (example B.13) according to general procedure II. Yellow solid. MS (ISP) 589.2 [(M−H)⁻]; mp 280° C.

Example 61

5-(4-Chloro-phenyl)-7-cyclopropyl-pyrazolo[1,5-a]pyrimidine-3-carboxylic acid [2-chloro-5-(2-hydroxy-1,1-dimethyl-ethylsulfamoyl)-thiophen-3-yl]-amide The title compound was prepared from 5-(4-chloro-phenyl)-7-cyclopropyl-pyrazolo[1,5-a]pyrimidine-3-carboxylic acid (example C.19) and 4-amino-5-chloro-thiophene-2-sulfonic acid (2-hydroxy-1,1-dimethyl-ethyl)-amide (example B.2) according to general procedure II. Pale-yellow solid. (ISN) 580.0 [(M−H)⁻]; mp 238-241° C.

Example 62

5-(4-Chloro-phenyl)-7-cyclopropyl-pyrazolo[1,5-a]pyrimidine-3-carboxylic acid [5-(2-hydroxy-1,1-dimethyl-ethylsulfamoyl)-4-methyl-thiazol-2-yl]-amide The title compound was prepared from 5-(4-chloro-phenyl)-7-cyclopropyl-pyrazolo[1,5-a]pyrimidine-3-carboxylic acid (example C.19) and 2-amino-4-methyl-thiazole-5-sulfonic acid (2-hydroxy-1,1-dimethyl-ethyl)-amide (example B.3) according to general procedure II. Pale-yellow solid. MS (ISN) 559.0 [(M−H)⁻]; mp 293-294° C.

Example 63

7-Difluoromethyl-5-(4-trifluoromethyl-phenyl)-pyrazolo[1,5-a]pyrimidine-3-carboxylic acid [5-(2-hydroxy-1-hydroxymethyl-ethylsulfamoyl)-4-methyl-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-hydroxy-1-hydroxymethyl-ethyl)-amide (example B.16) according to general procedure II. Light yellow solid. MS (ISP) 604.8 [(M−H)⁻]; mp 217° C.

Example 64

7-Trifluoromethyl-5-(4-trifluoromethyl-phenyl)-pyrazolo[1,5-a]pyrimidine-3-carboxylic acid [5-(2-hydroxy-1-hydroxymethyl-ethylsulfamoyl)-4-methyl-thiazol-2-yl]-amide The title compound was prepared from 7-trifluoromethyl-5-(4-trifluoromethyl-phenyl)-pyrazolo[1,5-a]pyrimidine-3-carboxylic acid (example C.1) and 2-amino-4-methyl-thiazole-5-sulfonic acid (2-hydroxy-1-hydroxymethyl-ethyl)-amide (example B. 16) according to general procedure II. Light yellow solid. MS (ISP) 623.1 [(M−H)⁻]; mp 215° C.

Example 65

7-Difluoromethyl-5-(4-trifluoromethyl-phenyl)-pyrazolo[1,5-a]pyrimidine-3-carboxylic acid [5-(2-amino-ethylsulfamoyl)-2-chloro-thiophen-3-yl]-amide The title compound was prepared from 7-difluoromethyl-5-(4-trifluoromethyl-phenyl)-pyrazolo[1,5-a]pyrimidine-3-carboxylic acid (example C.1) and [2-(4-amino-5-chlorothiophene-2-sulfonylamino)-ethyl]-carbamic acid tert-butyl ester (example B.17) according to general procedure II and subsequent removal of the protecting group with trifluoroacetic acid in dichloromethane at 0° C. for 3 h. Orange solid. MS (ISP) 595.0 [(M+H)$^+$]; mp 150° C.

Example 66

7-Difluoromethyl-5-(4-trifluoromethyl-phenyl)-pyrazolo[1,5-a]pyrimidine-3-carboxylic acid [(RS)-2-chloro-5-(3-hydroxy-pyrrolidine-1-sulfonyl)-thiophen-3-yl]-amide The title compound was prepared from 7-difluoromethyl-5-(4-trifluoromethyl-phenyl)-pyrazolo[1,5-a]pyrimidine-3-carboxylic acid (example C.1) and (RS)-1-(4-amino-5-chloro-thiophene-2-sulfonyl)-pyrrolidin-3-ol (example B.18) according to general procedure II. Yellow solid. MS (ISP) 622.2 [(M+H)$^+$]; mp 274° C.

Example 67

7-Trifluoromethyl-5-(4-trifluoromethyl-phenyl)-pyrazolo[1,5-a]pyrimidine-3-carboxylic acid [(RS)-2-chloro-5-(3-hydroxy-pyrrolidine-1-sulfonyl)-thiophen-3-yl]-amide The title compound was prepared from 7-trifluoromethyl-5-(4-trifluoromethyl-phenyl)-pyrazolo[1,5-a]pyrimidine-3-carboxylic acid (example C.1) and (RS)-1-(4-amino-5-chloro-thiophene-2-sulfonyl)-pyrrolidin-3-ol-(example B.18) according to general procedure II. Yellow solid. MS (ISP) 640.2 [(M+H)$^+$]; mp 270° C.

Example 68

7-Difluoromethyl-5-(4-trifluoromethyl-phenyl)-pyrazolo[1,5-a]pyrimidine-3-carboxylic acid [4-methyl-5-(4-methyl-piperazine-1-sulfonyl)-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and 4-methyl-5-(4-methyl-piperazine-1-sulfonyl)-thiazol-2-ylamine (example B.19) according to general procedure II.
Yellow solid. MS (ISP) 616.2 [(M+H)$^+$]; mp 269° C.

Example 69

7-Trifluoromethyl-5-(4-trifluoromethyl-phenyl)-pyrazolo[1,5-a]pyrimidine-3-carboxylic acid [4-methyl-5-(4-methyl-piperazine-1-sulfonyl)-thiazol-2-yl]-amide The title compound was prepared from 7-trifluoromethyl-5-(4-trifluoromethyl-phenyl)-pyrazolo[1,5-a]pyrimidine-3-carboxylic acid (example C.1) and 4-methyl-5-(4-methyl-piperazine-1-sulfonyl)-thiazol-2-ylamine (example B.19) according to general procedure II. Yellow solid. MS (ISP) 634.1 [(M+H)$^+$]; mp 273° C.

Example 70

7-Difluoromethyl-5-(4-trifluoromethyl-phenyl)-pyrazolo[1,5-a]pyrimidine-3-carboxylic acid {5-[(2-hydroxy-ethyl)-methyl-sulfamoyl]-4-methyl-thiazol-2-yl}-amide The title compound was prepared from 7-difluoromethyl-5-(4-trifluoromethyl-phenyl)-pyrazolo[1,5-a]pyrimidine-3-carboxylic acid (example C. 1) and 2-amino-4-methyl-thiazole-5-sulfonic acid (2-hydroxy-ethyl)-methyl-amide (example B.20) according to general procedure II.
Light yellow solid. MS (ISP) 591.1 [(M+H)$^+$]; mp 216° C.

Example 71

7-Trifluoromethyl-5-(4-trifluoromethyl-phenyl)-pyrazolo[1,5-a]pyrimidine-3-carboxylic acid {5-[(2-hydroxy-ethyl)-methyl-sulfamoyl]-4-methyl-thiazol-2-yl}-amide The title compound was prepared from 7-trifluoromethyl-5-(4-trifluoromethyl-phenyl)-pyrazolo[1,5-a]pyrimidine-3-carboxylic acid (example C. 1) and 2-amino-4-methyl-thiazole-5-sulfonic acid (2-hydroxy-ethyl)-methyl-amide (example B.20) according to general procedure II.
Yellow solid. MS (ISP) 609.0 [(M+H)$^+$]; mp 266° C.

Example 72

7-Difluoromethyl-5-(4-trifluoromethyl-phenyl)-pyrazolo[1,5-a]pyrimidine-3-carboxylic acid {2-chloro-5-[(2-hydroxy-ethyl)-methyl-sulfamoyl]-thiophen-3-yl}-amide The title compound was prepared from 7-difluoromethyl-5-(4-trifluoromethyl-phenyl)-pyrazolo[1,5-a]pyrimidine-3-carboxylic acid (example C. 1) and 4-amino-5-chloro-thiophene-2-sulfonic acid (2-hydroxy-ethyl)-methyl-amide (example B.21) according to general procedure II.
Light brown solid. MS (ISP) 607.8 [(M−H)$^−$]; mp 231° C.

Example 73

7-Difluoromethyl-5-(4-trifluoromethyl-phenyl)-pyrazolo[1,5-a]pyrimidine-3-carboxylic acid [2-chloro-5-(4-methyl-piperazine-1-sulfonyl)-thiophen-3-yl]-amide The title compound was prepared from 7-difluoromethyl-5-(4-trifluoromethyl-phenyl)-pyrazolo[1,5-a]pyrimidine-3-carboxylic acid (example C.1) and 2-chloro-5-(4-methyl-piperazine-1-sulfonyl)-thiophen-3-ylamine (example B.22) according to general procedure II.
Yellow solid. MS (ISP) 635.3 [(M+H)$^+$]; mp 293° C.

Example 74

7-Trifluoromethyl-5-(4-trifluoromethyl-phenyl)-pyrazolo[1,5-a]pyrimidine-3-carboxylic acid [2-chloro-5-(4-methyl-piperazine-1-sulfonyl)-thiophen-3-yl]-amide The title compound was prepared from 7-trifluoromethyl-5-(4-trifluoromethyl-phenyl)-pyrazolo[1,5-a]pyrimidine-3-carboxylic acid (example C.1) and 2-chloro-5-(4-methyl-piperazine-1-sulfonyl)-thiophen-3-ylamine (example B.22) according to general procedure II.

Yellow solid. MS (ISP) 653.3 [(M+H)$^+$]; mp 301° C.

Example 75

(RS)-7-Difluoromethyl-5-(4-trifluoromethyl-phenyl)-pyrazolo[1,5-a]pyrimidine-3-carboxylic acid [(RS)-5-(3-hydroxy-pyrrolidine-1-sulfonyl)-4-ethyl-thiazol-2-yl]-amide The title compound was prepared from 7-difluoromethyl-5-(4-trifluoromethyl-phenyl)-pyrazolo[1,5-a]pyrimidine-3-carboxylic acid (example C.1) and (RS)-1-(2-amino-4-methyl-thiazole-5-sulfonyl)-pyrrolidin-3-ol (example B.23) according to general procedure II. Light yellow solid. MS (ISP) 603.0 [(M+H)$^+$]; mp 286° C.

Example 76

7-Trifluoromethyl-5-(4-trifluoromethyl-phenyl)-pyrazolo[1,5-a]pyrimidine-3-carboxylic acid [(RS)-5-(3-hydroxy-pyrrolidine-1-sulfonyl)-4-methyl-thiazol-2-yl]-amide The title compound was prepared from 7-trifluoromethyl-5-(4-trifluoromethyl-phenyl)-pyrazolo[1,5-a]pyrimidine-3-carboxylic acid (example C.1) and (RS)-1-(2-amino-4-methyl-thiazole-5-sulfonyl)-pyrrolidin-3-ol (example B.23) according to general procedure II. Light yellow solid. MS (ISP) 621.0 [(M+H)$^+$]; mp 300° C.

Example 77

7-Trifluoromethyl-5-(4-trifluoromethyl-phenyl)-pyrazolo[1,5-a]pyrimidine-3-carboxylic acid {2-chloro-5-[(2-hydroxy-ethyl)-methyl-sulfamoyl]-thiophen-3-yl}-amide The title compound was prepared from 7-trifluoromethyl-5-(4-trifluoromethyl-phenyl)-pyrazolo[1,5-a]pyrimidine-3-carboxylic acid (example C. 1) and 4-amino-5-chloro-thiophene-2-sulfonic acid (2-hydroxy-ethyl)-methyl-amide (example B.21) according to general procedure II.

Yellow solid. MS (ISP) 628.1 [(M+H)$^+$]; mp 221° C.

Example 78

7-Trifluoromethyl-5-(4-trifluoromethyl-phenyl)-pyrazolo[1,5-a]pyrimidine-3-carboxylic acid [5-(2-amino-ethylsulfamoyl)-2-chloro-thiophen-3-yl]-amide The title compound was prepared from 7-trifluoromethyl-5-(4-trifluoromethyl-phenyl)-pyrazolo[1,5-a]pyrimidine-3-carboxylic acid (example C.1) and [2-(4-amino-5-chloro-thiophene-2-sulfonylamino)-ethyl]-carbamic acid tert-butyl ester (example B.17) according to general procedure II and subsequent removal of the protecting group with trifluoroacetic acid in dichloromethane at 0° C. for 3 h. Yellow solid. MS (ISP) 611.0 [(M−H)$^−$]; mp 195° C.

Preparation of Pharmaceutical Compositions Comprising Compounds of the Invention:

Example I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula (I)

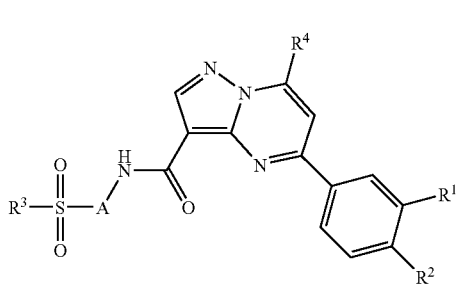

(I)

wherein
A is selected from the group consisting of:

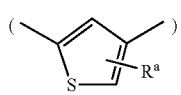
(a)

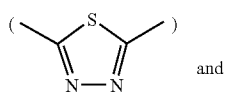
and
(b)

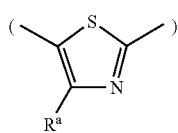
(c)

$R^a$ is H, halo or $C_{1-6}$-alkyl;

$R^1$ is H, halo, $C_{1-6}$-alkoxy, $C_{1-6}$-alkyl, $C_{1-6}$-haloalkyl, or $C_{1-6}$-haloalkoxy;

$R^2$ is halogen, or $C_{1-6}$-haloalkyl;

$R^3$ is $C_{1-6}$-alkyl optionally substituted by hydroxy,
or is $NR^bR^c$ wherein $R^b$ and $R^c$ are independently selected from the group consisting of:
H, $C_{3-8}$-cycloalkyl, aryl, heteroaryl having from 5 to 12 ring atoms, and $C_{1-6}$-alkyl which is optionally substituted by one or more substituent(s) selected from the group consisting of halo, hydroxy, $C_{3-8}$-cycloalkyl, aryl, heteroaryl having from 5 to 12 ring atoms and —$NR^{b'}R^{c'}$, wherein $R^{b'}$ and $R^{c'}$ are each independently selected from the group consisting of H and $C_{1-6}$-alkyl;
or $R^b$ and $R^c$ can, together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl; and $R^4$ is H, straight $C_{1-6}$-alkyl, $C_{1-6}$-haloalkyl or $C_{3-4}$-cycloalkyl;

or a pharmaceutically acceptable salt thereof.

2. The compound of claim 1 wherein:
A is selected from the group consisting of:

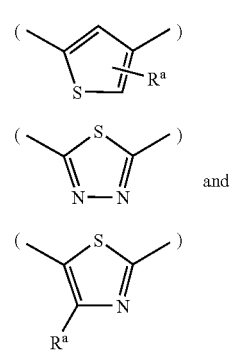

(a)

(b)
and (c)

wherein
$R^a$ is H, halo or $C_{1-6}$-alkyl;
$R^1$ is H, halo, $C_{1-6}$-alkoxy, $C_{1-6}$-alkyl, $C_{1-6}$-haloalkyl, or $C_{1-6}$-haloalkoxy;
$R^2$ is halogen or $C_{1-6}$-haloalkyl;
$R^3$ is $NR^bR^c$ wherein $R^b$ and $R^c$ are each independently selected from the group consisting of: H; $C_{1-6}$-allyl which is optionally substituted by one or more substituent(s) selected from the group consisting of hydroxy and —$NR^{b'}R^{c'}$, wherein $R^{b'}$ and $R^{c'}$ are each independently selected from the group consisting of H and $C_{1-6}$-alkyl; and
$R^4$ is $C_{1-6}$-haloalkyl or $C_{3-4}$-cycloalkyl;
or a pharmaceutically acceptable salt thereof.

3. The compound of claim 1, wherein
A is selected from the group consisting of

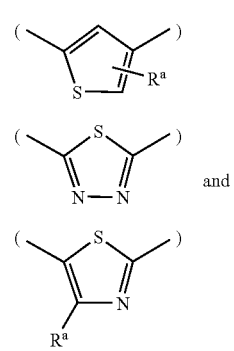

(a)

(b)
and (c)

$R^a$ is H, Cl, or methyl;
$R^1$ is H, Cl, MeO, EtO, methyl, $CHF_2$, $CF_3$, or $CF_3CH_2O$;
$R^2$ is Cl, or $CF_3$;
$R^3$ is $NR^bR^c$ wherein $R^b$ and $R^c$ are each independently selected from the group consisting of H, methyl, ethyl, i-propyl, or t-butyl, each of which is optionally substituted by one or more substituent selected from the group consisting of hydroxy and —$NR^{b'}R^{c'}$, wherein $R^{b'}$ and $R^{c'}$ are each independently selected from the group consisting of H and methyl; and
$R^4$ is $CHF_2$, $CF_3$, or cyclopropyl
or a pharmaceutically acceptable salt thereof.

4. The compound of claim 1, having formula (Ia):

$$\text{(Ia)}$$

or a pharmaceutically acceptable salt thereof.

5. The compound of claim 4, selected from the group consisting of:

- 7-Difluoromethyl-5-(4-trifluoromethyl-phenyl)-pyrazolo[1,5-a]pyrimidine-3-carboxylic acid (2-chloro-5-sulfamoyl-thiophen-3-yl)-amide;
- 7-Trifluoromethyl-5-(4-trifluoromethyl-phenyl)-pyrazolo[1,5-a]pyrimidine-3-carboxylic acid (2-chloro-5-sulfamoyl-thiophen-3-yl)-amide;
- 7-Difluoromethyl-5-(4-trifluoromethyl-phenyl)-pyrazolo[1,5-a]pyrimidine-3-carboxylic acid [2-chloro-5-(2-hydroxy-1,1-dimethyl-ethylsulfamoyl)-thiophen-3-yl]-amide;
- 7-Trifluoromethyl-5-(4-trifluoromethyl-phenyl)-pyrazolo[1,5-a]pyrimidine-3-carboxylic acid [2-chloro-5-(2-hydroxy-1,1-dimethyl-ethylsulfamoyl)-thiophen-3-yl]-amide;
- 5-(4-Chloro-phenyl)-7-trifluoromethyl-pyrazolo[1,5-a]pyrimidine-3-carboxylic acid (2-chloro-5-sulfamoyl-thiophen-3-yl)-amide;
- 5-(3-Ethoxy-4-trifluoromethyl-phenyl)-7-trifluoromethyl-pyrazolo[1,5-a]pyrimidine-3-carboxylic acid (2-chloro-5-sulfamoyl-thiophen-3-yl)-amide;
- 5-(3-Methyl-4-trifluoromethyl-phenyl)-7-trifluoromethyl-pyrazolo[1,5-a]pyrimidine-3-carboxylic acid (2-chloro-5-sulfamoyl-thiophen-3-yl)-amide;
- 5-(4-Chloro-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide; and
- 5-(3-Ethoxy-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide.

6. The compound of claim 4, selected from the group consisting of:

- 5-(3-Methyl-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
- 5-[3-(2,2,2-Trifluoro-ethoxy)-4-trifluoromethyl-phenyl]-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
- 5-(3-Chloro-4-trifluoromethyl-phenyl)-7-trifluoromethyl-pyrazolo[1,5-a]pyrimidine-3-carboxylic acid [2-chloro-5-(2-hydroxy-1,1-dimethyl-ethylsulfamoyl)-thiophen-3-yl]-amide;
- 7-Difluoromethyl-5-(4-trifluoromethyl-phenyl)-pyrazolo[1,5-a]pyrimidine-3-carboxylic acid [2-chloro-5-(2-hydroxy-1-hydroxymethyl-ethylsulfamoyl)-thiophen-3-yl]-amide;
- 7-Trifluoromethyl-5-(4-trifluoromethyl-phenyl)-pyrazolo[1,5-a]pyrimidine-3-carboxylic acid [2-chloro-5-(2-hydroxy-1-hydroxymethyl-ethylsulfamoyl)-thiophen-3-yl]-amide;
- 7-Difluoromethyl-5-(4-trifluoromethyl-phenyl)-pyrazolo[1,5-a]pyrimidine-3-carboxylic-acid {5-[bis-(2-hydroxy-ethyl)-sulfamoyl]-2-chloro-thiophen-3-yl}-amide;
- 7-Trifluoromethyl-5-(4-trifluoromethyl-phenyl)-pyrazolo[1,5-a]pyrimidine-3-carboxylic acid {5-[bis-(2-hydroxy-ethyl)-sulfamoyl]-2-chloro-thiophen-3-yl}-amide;
- 7-Trifluoromethyl-5-(4-trifluoromethyl-phenyl)-pyrazolo[1,5-a]pyrimidine-3-carboxylic acid [2-chloro-5-(2-hydroxy-ethylsulfamoyl)-thiophen-3-yl]-amide; and
- 7-Difluoromethyl-5-(4-trifluoromethyl-phenyl)-pyrazolo[1,5-a]pyrimidine-3-carboxylic acid [2-chloro-5-(2-hydroxy-1-hydroxymethyl-1-methyl-ethylsulfamoyl)-thiophen-3-yl]-amide.

7. The compound of claim 4, selected from the group consisting of:

- 7-Trifluoromethyl-5-(4-trifluoromethyl-phenyl)-pyrazolo[1,5-a]pyrimidine-3-carboxylic acid [2-chloro-5-(2-hydroxy-1-hydroxymethyl-1-methyl-ethylsulfamoyl)-thiophen-3-yl]-amide;
- 7-Difluoromethyl-5-(4-trifluoromethyl-phenyl)-pyrazolo[1,5-a]pyrimidine-3-carboxylic acid [2-chloro-5-(2-hydroxy-ethylsulfamoyl)-thiophen-3-yl]-amide;
- 7-Trifluoromethyl-5-(4-trifluoromethyl-phenyl)-pyrazolo[1,5-a]pyrimidine-3-carboxylic acid (2-methyl-5-sulfamoyl-thiophen-3-yl)-amide;
- 7-Difluoromethyl-5-(4-trifluoromethyl-phenyl)-pyrazolo[1,5-a]pyrimidine-3-carboxylic acid (2-methyl-5-sulfamoyl-thiophen-3-yl)-amide;
- 7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-2-methyl-thiophen-3-yl]-amide;
- 7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-2-methyl-thiophen-3-yl]-amide;
- 7-Difluoromethyl-5-(4-trifluoromethyl-phenyl)-pyrazolo[1,5-a]pyrimidine-3-carboxylic acid [2-chloro-5-(2-dimethylamino-ethylsulfamoyl)-thiophen-3-yl]-amide;
- 7-Trifluoromethyl-5-(4-trifluoromethyl-phenyl)-pyrazolo[1,5-a]pyrimidine-3-carboxylic acid [2-chloro-5-(2-dimethylamino-ethylsulfamoyl)-thiophen-3-yl]-amide; and
- 5-(3-Ethoxy-4-trifluoromethyl-phenyl)-7-trifluoromethyl-pyrazolo[1,5-a]pyrimidine-3-carboxylic acid [2-chloro-5-(2-hydroxy-ethylsulfamoyl)-thiophen-3-yl]-amide.

8. The compound of claim 4, selected from the group consisting of:

- 5-(4-Chloro-phenyl)-7-cyclopropyl-pyrazolo[1,5-a]pyrimidine-3-carboxylic acid [2-chloro-5-(2-hydroxy-1,1-dimethyl-ethylsulfamoyl)-thiophen-3-yl]-amide;

7-Difluoromethyl-5-(4-trifluoromethyl-phenyl)-pyrazolo[1,5-a]pyrimidine-3-carboxylic acid [5-(2-amino-ethylsulfamoyl)-2-chloro-thiophen-3-yl]-amide;

7-Difluoromethyl-5-(4-trifluoromethyl-phenyl)-pyrazolo[1,5-a]pyrimidine-3-carboxylic acid [(R/S)-2-chloro-5-(3-hydroxy-pyrrolidinyl-1-sulfonyl)-thiophen-3-yl]-amide;

7-Trifluoromethyl-5-(4-trifluoromethyl-phenyl)-pyrazolo[1,5-a]pyrimidine-3-carboxylic acid [(R/S)-2-chloro-5-(3-hydroxy-pyrrolidinyl-1-sulfonyl)-thiophen-3-yl]-amide;

7-Difluoromethyl-5-(4-trifluoromethyl-phenyl)-pyrazolo[1,5-a]pyrimidine-3-carboxylic acid {2-chloro-5-[(2-hydroxy-ethyl)-methyl-sulfamoyl]-thiophen-3-yl}-amide;

7-Difluoromethyl-5-(4-trifluoromethyl-phenyl)-pyrazolo[1,5-a]pyrimidine-3-carboxylic acid [2-chloro-5-(4-methyl-piperzinyl-1-sulfonyl)-thiophen-3-yl]-amide;

7-Trifluoromethyl-5-(4-trifluoromethyl-phenyl)-pyrazolo[1,5-a]pyrimidine-3-carboxylic acid [2-chloro-5-(4-methyl-piperzinyl-1-sulfonyl)-thiophen-3-yl]-amide;

7-Trifluoromethyl-5-(4-trifluoromethyl-phenyl)-pyrazolo[1,5-a]pyrimidine-3-carboxylic acid {2-chloro-5-[(2-hydroxy-ethyl)-methyl-sulfamoyl]-thiophen-3-yl}-amide; and 7-Trifluoromethyl-5-(4-trifluoromethyl-phenyl)-pyrazolo[1,5-a]pyrimidine-3-carboxylic acid [5-(2-amino-ethylsulfamoyl)-2-chloro-thiophen-3-yl]-amide.

9. The compound of claim 1, having formula (Ib):

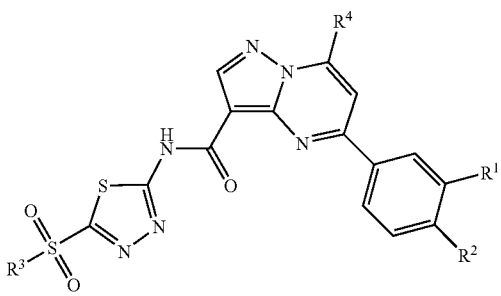

(Ib)

or a pharmaceutically acceptable salt thereof.

10. The compound of claim 9, selected from the group consisting of:

7-Difluoromethyl-5-(4-trifluoromethyl-phenyl)-pyrazolo[1,5-a]pyrimidine-3-carboxylic acid (5-sulfamoyl-[1,3,4]thiadiazol-2-yl)-amide; and 7-Trifluoromethyl-5-(4-trifluoromethyl-phenyl)-pyrazolo[1,5-a]pyrimidine-3-carboxylic acid (5-sulfamoyl-[1,3,4]thiadiazol-2-yl)-amide.

11. The compound of claim 1, having formula (Ic):

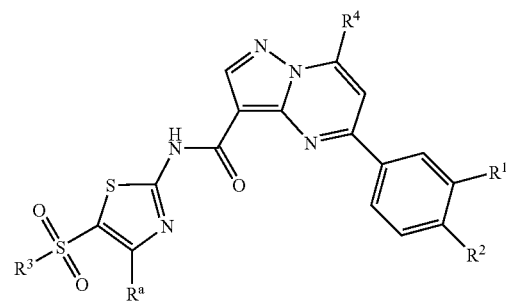

(Ic)

or a pharmaceutically acceptable salt thereof.

12. The compound of claim 11, selected from the group consisting of:

7-Difluoromethyl-5-(4-trifluoromethyl-phenyl)-pyrazolo[1,5-a]pyrimidine-3-carboxylic acid (4-methyl-5-sulfamoyl-thiazol-2-yl)-amide;

7-Trifluoromethyl-5-(4-trifluoromethyl-phenyl)-pyrazolo[1,5-a]pyrimidine-3-carboxylic acid (4-methyl-5-sulfamoyl-thiazol-2-yl)-amide;

7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide;

5-(4-Chloro-phenyl)-7-trifluoromethyl-pyrazolo[1,5-a]pyrimidine-3-carboxylic acid (4-methyl-5-sulfamoyl-thiazol-2-yl)-amide;

5-(3-Ethoxy-4-trifluoromethyl-phenyl)-7-trifluoromethyl-pyrazolo[1,5-a]pyrimidine-3-carboxylic acid (4-methyl-5-sulfamoyl-thiazol-2-yl)-amide;

5-(3-Methyl-4-trifluoromethyl-phenyl)-7-trifluoromethyl-pyrazolo[1,5-a]pyrimidine-3-carboxylic acid (4-methyl-5-sulfamoyl-thiazol-2-yl)-amide;

5-(4-Chloro-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-(3-Ethoxy-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide; and 5-(3-Methyl-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide.

13. The compound of claim 11, selected from the group consisting of:

5-(3-Chloro-4-trifluoromethyl-phenyl)-7-trifluoromethyl-pyrazolo[1,5-a]pyrimidine-3-carboxylic acid (4-methyl-5-sulfamoyl-thiazol-2-yl)-amide;

5-(3,4-Dichloro-phenyl)-7-trifluoromethyl-pyrazolo[1,5-a]pyrimidine-3-carboxylic acid (4-methyl-5-sulfamoyl-thiazol-2-yl)-amide;

5-[3-(2,2,2-Trifluoro-ethoxy)-4-trifluoromethyl-phenyl]-7-trifluoromethyl-pyrazolo[1,5-a]pyrimidine-3-carboxylic acid (4-methyl-5-sulfamoyl-thiazol-2-yl)-amide;

5-(3-Chloro-4-trifluoromethyl-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-(3,4-Dichloro-phenyl)-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

5-[3-(2,2,2-Trifluoro-ethoxy)-4-trifluoromethyl-phenyl]-7-trifluoromethyl-pyrazolo[1,5-a]pyrimidine-3-carboxylic acid [5-(2-hydroxy-1,1-dimethyl-ethylsulfamoyl)-4-methyl-thiazol-2-yl]-amide;

7-Difluoromethyl-5-(3-methyl-4-trifluoromethyl-phenyl)-pyrazolo[1,5-a]pyrimidine-3-carboxylic acid (4-methyl-5-sulfamoyl-thiazol-2-yl)-amide;

7-Difluoromethyl-5-(3-methyl-4-trifluoromethyl-phenyl)-pyrazolo[1,5-a]pyrimidine-3-carboxylic acid [5-(2-hydroxy-1,1-dimethyl-ethylsulfamoyl)-4-methyl-thiazol-2-yl]-amide; and 7-Difluoromethyl-5-(4-trifluoromethyl-phenyl)-pyrazolo[1,5-a]pyrimidine-3-carboxylic acid {5-[bis-(2-hydroxy-ethyl)-sulfamoyl]-4-methyl-thiazol-2-yl}-amide.

14. The compound of claim 11, selected from the group consisting of:

7-Trifluoromethyl-5-(4-trifluoromethyl-phenyl)-pyrazolo[1,5-a]pyrimidine-3-carboxylic acid {5-[bis-(2-hydroxy-ethyl)-sulfamoyl]-4-methyl-thiazol-2-yl}-amide;

7-Trifluoromethyl-5-(4-trifluoromethyl-phenyl)-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid[5-(2-hydroxy-1-hydroxymethyl-1-methyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid[5-(2-hydroxy-ethylsulfamoyl)-4-methyl-thiazol-2-yl]-amide;

7-Trifluoromethyl-5-(4-trifluoromethyl-phenyl)-pyrazolo[1,5-a]pyrimidine-3-carboxylic acid [5-(2-hydroxy-ethylsulfamoyl)-4-methyl-thiazol-2-yl]-amide;

7-Trifluoromethyl-5-(4-trifluoromethyl-phenyl)-pyrazolo[1,5-a]pyrimidine-3-carboxylic acid (5-sulfamoyl-thiazol-2-yl)-amide;

7-Difluoromethyl-5-(4-trifluoromethyl-phenyl)-pyrazolo[1,5-a]pyrimidine-3-carboxylic acid (5-sulfamoyl-thiazol-2-yl)-amide;

5-(3-Ethoxy-4-trifluoromethyl-phenyl)-7-trifluoromethyl-pyrazolo[1,5-a]pyrimidine-3-carboxylic acid [5-(2-hydroxy-1-hydroxymethyl-1-methyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-dimethylamino-ethylsulfamoyl)-4-methyl-thiazol-2-yl]-amide; and 7-Trifluoromethyl-5-(4-trifluoromethyl-phenyl)-pyrazolo[1,5-a]pyrimidine-3-carboxylic acid [5-(2-dimethylamino-ethylsulfamoyl)-4-methyl-thiazol-2-yl]-amide.

15. The compound of claim 11, selected from the group consisting of:

7-Difluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-thiazol-2-yl]-amide;

7-Trifluoromethyl-5-(4-trifluoromethyl-phenyl)-pyrazolo[1,5-a]pyrimidine-3-carboxylic acid [5-(2-hydroxy-1,1-dimethyl-ethylsulfamoyl)-thiazol-2-yl]-amide;

5-(4-Chloro-phenyl)-7-cyclopropyl-pyrazolo[1,5-a]pyrimidine-3-carboxylic acid [5-(2-hydroxy-1,1-dimethyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [5-(2-hydroxy-1-hydroxymethyl-ethylsulfamoyl)-4-methyl-thiazol-2-yl]-amide;

7-Trifluoromethyl-5-(4-trifluoromethyl-phenyl)-pyrazolo[1,5-a]pyrimidine-3-carboxylic acid [5-(2-hydroxy-1-hydroxymethyl-ethylsulfamoyl)-4-methyl-thiazol-2-yl]-amide;

7-Difluoromethyl-5-(4-trifluoromethyl-phenyl)-pyrazolo[1,5-a]pyrimidine-3-carboxylic acid [4-methyl-5-(4-methyl-piperzinyl-1-sulfonyl)-thiazol-2-yl]-amide;

7-Trifluoromethyl-5-(4-trifluoromethyl-phenyl)-pyrazolo[1,5-a]pyrimidine-3-carboxylic acid [4-methyl-5-(4-methyl-piperzinyl-1-sulfonyl)-thiazol-2-yl]-amide;

7-Difluoromethyl-5-(4-trifluoromethyl-phenyl)-pyrazolo[1,5-a]pyrimidine-3-carboxylic acid {5-[(2-hydroxy-ethyl)-methyl-sulfamoyl]-4-methyl-thiazol-2-yl}-amide;

7-Trifluoromethyl-5-(4-trifluoromethyl-phenyl)-pyrazolo[1,5-a]pyrimidine-3-carboxylic acid {5-[(2-hydroxy-ethyl)-methyl-sulfamoyl]-4-methyl-thiazol-2-yl}-amide;

(R/S)-7-Difluoromethyl-5-(4-trifluoromethyl-phenyl)-pyrazolo[1,5-a]pyrimidine-3-carboxylic acid [(R/S)-5-(3-hydroxy-pyrrolidinyl-1-sulfonyl)-4-methyl-thiazol-2-yl]-amide; and 7-Trifluoromethyl-5-(4-trifluoromethyl-phenyl)-pyrazolo[1,5-a]pyrimidine-3-carboxylic acid [(R/S)-5-(3-hydroxy-pyrrolidinyl-1-sulfonyl)-4-methyl-thiazol-2-yl]-amide.

16. The compound of claim 1, wherein $R^3$ is $C_{1-6}$-alkyl optionally substituted by hydroxyl.

17. The compound of claim 1, wherein $R^3$ is $NR^bR^c$ wherein $R^b$ and $R^c$ are independently selected from the group consisting of:

H, $C_{3-8}$-cycloalkyl, aryl, heteroaryl having from 5 to 12 ring atoms, and $C_{1-6}$-alkyl which is optionally substituted by one or more substituent(s) selected from the group consisting of halo, hydroxy, $C_{3-8}$-cycloalkyl, aryl, heteroaryl having from 5 to 12 ring atoms and —$NR^{b'}R^{c'}$, wherein $R^{b'}$ and $R^{c'}$ are each independently selected from the group consisting of H and $C_{1-6}$-alkyl; or $R^b$ and $R^c$ can, together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl.

18. The compound of claim 17, wherein $R^b$ and $R^c$ are hydrogen.

19. The compound of claim 17, wherein $R^b$ and $R^c$ are each independently $C_{1-6}$-alkyl, optionally substituted by one or more substituent(s) selected from the group consisting of halo, hydroxy, and $C_{3-8}$-cycloalkyl.

20. The compound of claim 17, wherein $R^b$ and $R^c$ are each independently $C_{1-6}$-alkyl, optionally substituted by —$NR^{b'}R^{c'}$, wherein $R^{b'}$ and $R^{c'}$ are each independently selected from the group consisting of H and $C_{1-6}$-alkyl.

21. The compound of claim 17, wherein $R^b$ and $R^c$ together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl.

22. A pharmaceutical composition comprising a therapeutically effective amount of a compound of formula (I)

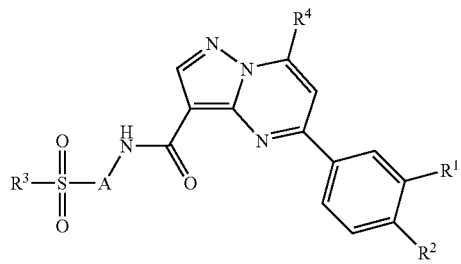

wherein

A is selected from the group consisting of:

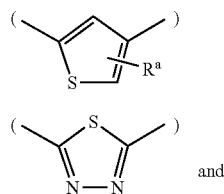

and

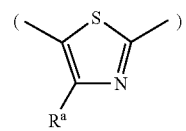

$R^a$ is H, halo or $C_{1-6}$-alkyl;

$R^1$ is H, halo, $C_{1-6}$-alkoxy, $C_{1-6}$-alkyl, $C_{1-6}$-haloalkyl, or $C_{1-6}$-haloalkoxy;

$R^2$ is halogen, or $C_{1-6}$-haloalkyl;

$R^3$ is $C_{1-6}$-alkyl optionally substituted by hydroxy; or is $NR^bR^c$ wherein $R^b$ and $R^c$ are independently selected from the group consisting of:

H, $C_{3-8}$-cycloalkyl, aryl, heteroaryl having from 5 to 12 ring atoms, and $C_{1-6}$-alkyl which is optionally substituted by one or more substituent(s) selected from the group consisting of halo, hydroxy, $C_{3-8}$-cycloalkyl, aryl, heteroaryl having from 5 to 12 ring atoms and $-NR^{b'}R^{c'}$, wherein $R^{b'}$ and $R^{c'}$ are each independently selected from the group consisting of H and $C_{1-6}$-alkyl;

or $R^b$ and $R^c$ can, together with the nitrogen atom to which they are attached, form an optionally substituted heterocyclic group having 5 to 12 ring atoms, wherein the substituents are selected from the group consisting of halo, hydroxy, $C_{1-6}$-alkyl and $C_{1-6}$-haloalkyl; and $R^4$ is H, straight $C_{1-6}$-alkyl, $C_{1-6}$-haloalkyl or $C_{3-4}$-cycloalkyl;

or a pharmaceutically acceptable salt thereof and a pharmaceutically acceptable carrier.

* * * * *